US012775011B2

(12) United States Patent
Hu et al.

(10) Patent No.: US 12,775,011 B2
(45) Date of Patent: Oct. 27, 2026

(54) CLICKABLE AND CLEAVABLE SENSING SURFACE AND METHOD OF MAKING THE SAME

(71) Applicant: DrinkSavvy, Inc., Brooklyn, NY (US)

(72) Inventors: Min Hu, Brooklyn, NY (US); Lilian Lamech, Brooklyn, NY (US); Jacob Trevino, Brooklyn, NY (US); Brendan Walker, Brooklyn, NY (US)

(73) Assignee: Chemeleon Inc., Brooklyn, NY (US)

( * ) Notice: Subject to any disclaimer, the term of this patent is extended or adjusted under 35 U.S.C. 154(b) by 414 days.

(21) Appl. No.: 18/487,555

(22) Filed: Oct. 16, 2023

(65) Prior Publication Data

US 2024/0125778 A1 Apr. 18, 2024

Related U.S. Application Data

(60) Provisional application No. 63/379,706, filed on Oct. 14, 2022.

(51) Int. Cl.

| | |
|---|---|
| ***G01N 33/543*** | (2006.01) |
| ***C12N 9/22*** | (2006.01) |
| ***C12N 15/11*** | (2006.01) |
| ***C12Q 1/6825*** | (2018.01) |
| ***G01N 33/53*** | (2006.01) |
| *G01N 21/78* | (2006.01) |

(52) U.S. Cl.

CPC ......... *G01N 33/54373* (2013.01); *C12N 9/22* (2013.01); *C12N 15/11* (2013.01); *C12Q 1/6825* (2013.01); *G01N 33/5308* (2013.01); *C12N 2310/20* (2017.05); *G01N 21/78* (2013.01)

(58) Field of Classification Search

None

See application file for complete search history.

(56) References Cited

U.S. PATENT DOCUMENTS

| | | | | |
|---|---|---|---|---|
| 11,717,831 B2 * | 8/2023 | Hu | B01L 3/5085 436/24 |
| 2002/0094533 A1 * | 7/2002 | Hess | B01J 19/0046 29/17.2 |
| 2019/0317011 A1 * | 10/2019 | Hu | G01N 21/77 |
| 2023/0296614 A1 * | 9/2023 | Hu | G01N 33/52 436/87 |
| 2024/0068018 A1 * | 2/2024 | Hu | C12Q 1/6844 |
| 2026/0104410 A1 * | 4/2026 | Hu | G01N 33/54306 |

* cited by examiner

*Primary Examiner* — Ann Montgomery

(74) *Attorney, Agent, or Firm* — Michael T. Abramson; Jordan IP Law, LLC

(57) ABSTRACT

A sensor, a method of manufacture, and a method of use for detecting an analyte of interest in a fluid sample. The sensor may include a structure that may include a plurality of walls that define a plurality of air gaps in the structure, wherein the plurality of walls may include a plurality of surfaces. The sensor may further include a hydrophobic clickable layer, wherein the hydrophobic clickable layer may be coated on the plurality of walls. The sensor may further include a binding material, wherein the binding material may be coated on the plurality of walls to bind to an analyte of interest. An initial surface energy of at least a portion of the plurality of surfaces of the plurality of walls may change when the analyte of interest binds with the binding material.

29 Claims, 9 Drawing Sheets

CLICKABLE AND CLEAVABLE SENSING SURFACE AND METHOD OF MAKING THE SAME

RELATED CASES

This application claims the benefit of U.S. Provisional Application No. 63/379,706, filed on 14 Oct. 2022, the contents of which are all incorporated by reference.

BACKGROUND

Generally, wetting based sensors typically require hydrophobic components to be immobilized on the sensor surface to enable an effective signal readout upon analyte binding; however, the hydrophobic components may require organic solvents to dissolve and process, which might not be compatible with the some molecular receptors that normally dissolve well only in aqueous solution.

SUMMARY

In one example implementation, a sensor for detecting an analyte of interest in a fluid sample may include but is not limited to a structure that may include a plurality of walls that define a plurality of air gaps in the structure, wherein the plurality of walls may include a plurality of surfaces. The sensor may further include a hydrophobic clickable layer, wherein the hydrophobic clickable layer may be coated on the plurality of walls. The sensor may further include a binding material, wherein the binding material may be coated on the plurality of walls to bind to an analyte of interest. An initial surface energy of at least a portion of the plurality of surfaces of the plurality of walls may change when the analyte of interest binds with the binding material.

One or more of the following example features may be included. The structure may include at least one of a micrometer scaled structure and a nanometer scaled structure. At least one of the micrometer scaled structure and the nanometer scaled structure may include a reentrant structure. The hydrophobic clickable layer may include a hydrophobic component to enable wetting based sensing, wherein the hydrophobic clickable layer may further include clickable components to immobilize the binding material via a click chemistry reaction. The hydrophobic component and the clickable components may be co-immobilized on the plurality of walls via a coupling chemistry process. The coupling chemistry process may include a silane coupling agent. The coupling chemistry process may include a glutaraldehyde conjugation crosslinker. The coupling chemistry process may include an NHS-EDC carbodiimide crosslinking chemistry. The hydrophobic components may include one of alkanes, fats, fluorocarbons, and fluorinated molecules. The clickable components may include clickable groups of one of azide, alkyne, thiol, alkene, tetrazine, trans-cyclooctene, bicyclo[6.1.0]nonyne, Dibenzocyclooctyne, and Trans-Cyclooctene. The click chemistry reaction may occur in aqueous solution. The binding material may include a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials. The change of the initial surface energy of at least the portion of the plurality of surfaces of the plurality of walls may be visually detectable with an instrument. The change of the initial surface energy of at least the portion of the plurality of surfaces of the plurality of walls may be visually detectable with a naked eye. The sensor may further include a colorimetric reporter, wherein the change of the initial surface energy of at least the portion of the plurality of surfaces of the plurality of walls may be visually detectable with a color change.

In another example implementation, a method of manufacturing a sensor for detecting an analyte of interest in a fluid sample may include but is not limited to providing a structure that may include a plurality of walls that define a plurality of air gaps in the structure, wherein the plurality of walls may include a plurality of surfaces. The plurality of walls may be coated with a hydrophobic clickable layer. The plurality of walls may be coated with a binding material to bind to an analyte of interest. An initial surface energy of at least a portion of the plurality of surfaces of the plurality of walls may change when the analyte of interest binds with the binding material.

One or more of the following example features may be included. The structure may include at least one of a micrometer scaled structure and a nanometer scaled structure. At least one of the micrometer scaled structure and the nanometer scaled structure may include a reentrant structure. The hydrophobic clickable layer may include a hydrophobic component to enable wetting based sensing, wherein the hydrophobic clickable layer may further include clickable components to immobilize the binding material via a click chemistry reaction. The hydrophobic component and the clickable components may be co-immobilized on the plurality of walls via a coupling chemistry process. The coupling chemistry process may include a silane coupling agent. The coupling chemistry process may include a glutaraldehyde conjugation crosslinker. The coupling chemistry process may include an NHS-EDC carbodiimide crosslinking chemistry. The hydrophobic components may include one of alkanes, fats, fluorocarbons, and fluorinated molecules. The clickable components may include clickable groups of one of azide, alkyne, thiol, alkene, tetrazine, trans-cyclooctene, bicyclo[6.1.0]nonyne, Dibenzocyclooctyne, and Trans-Cyclooctene. The click chemistry reaction may occur in aqueous solution. The binding material may include a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials. The change of the initial surface energy of at least the portion of the plurality of surfaces of the plurality of walls may be visually detectable with an instrument. The change of the initial surface energy of at least the portion of the plurality of surfaces of the plurality of walls may be visually detectable with a naked eye. The sensor may further include a colorimetric reporter, wherein the change of the initial surface energy of at least the portion of the plurality of surfaces of the plurality of walls may be visually detectable with a color change. A colorimetric reporter may be provided, wherein the change of the initial surface energy of at least the portion of the plurality of surfaces of the plurality of walls is visually detectable with a color change via the colorimetric reporter.

In another example implementation, a method of detecting an analyte of interest may include but is not limited to contacting the sensor described throughout with a sample.

An initial surface energy of at least a portion of the plurality of surfaces of the plurality of walls may change when the analyte of interest is present in the sample. A first mode may transition to a second mode based upon, at least in part, changing the initial surface energy.

In another example implementation, a sensor for detecting an analyte of interest in a sample may include but is not limited to a structural component grown on a surface from an initiator associated with a nucleic acid linker that is tethered to the surface, wherein a color of the surface may change upon growth of the structural component. The sensor may further include a surface associated with a ribonucleoprotein (RNP) complex that may include a CRISPR associated (Cas) nuclease, a guide RNA (gRNA) that may include a region that binds to the Cas nuclease, and a region that is complementary to a target nucleic acid sequence. When the target nucleic acid sequence contacts the gRNA, the gRNA may bind to the target nucleic acid sequence, the RNP complex may cleave the nucleic acid linker and may release the structural component grown on the surface, and may produce a detectable signal indicative of the target nucleic acid sequence being present.

One or more of the following example features may be included. The structural component may be a thin film. The structural component may be a patterned nanostructure and a nanoparticle. The initiator may be a polymerization initiator. The nucleic acid linker may be one of a single-stranded DNA (ssDNA), double-stranded DNA (dsDNA), and RNA. The target nucleic acid may be one of a single-stranded DNA (ssDNA), double-stranded DNA (dsDNA), and RNA. The Cas nuclease may be a type V Cas nuclease. The type V Cas nuclease may be one of Cas12a (Cpf1), Cas12b (C2c1), Cas12d, Cas12f (Cas14), and Cas12g. The Cas nuclease may be a type VI Cas nuclease. The type VI Cas nuclease may be one of Cas13a (C2c2), Cas13b, and Cas13d. The detectable signal may be visually detected by an instrument. The detectable signal may be visually detected by a naked eye. The detectable signal may be generated from destruction of at least a portion of a structural color indicator.

A method of detecting an analyte of interest may include but is not limited to contacting the sensor described throughout with a sample. When the analyte of interest is present in the sample, the nucleic acid linker may be cleaved, the structural component grown on the surface may be released, and a detectable signal indicative of the target nucleic acid sequence being present in the sample may be produced.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

In the drawings, like reference characters/symbols may generally refer to the same parts throughout the different views. For the purposes of clarity, not every component may be labeled in every drawing. Also, the drawings are not necessarily to scale, emphasis instead generally being placed upon showing the principles of the disclosure.

In the following description, various embodiments of the present disclosure are described with reference to the following drawings, in which.

Like reference symbols in the various drawings may indicate like elements.

DETAILED DESCRIPTION

Figure 1:
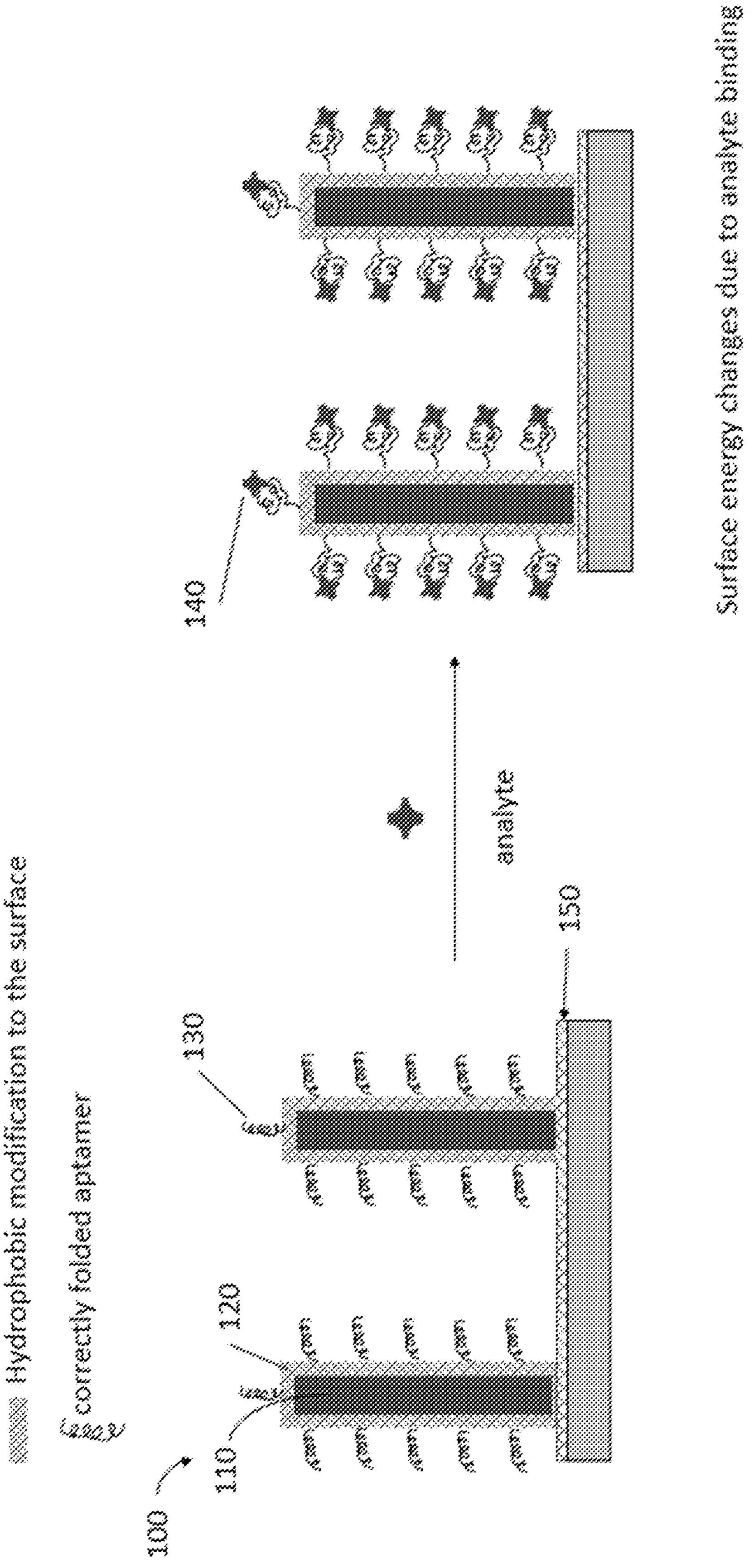
FIG. 1 shows an example sensor structure with integrated functional components for target binding in accordance with some embodiments of the present disclosure.

In one example implementation, a sensor for detecting an analyte of interest in a fluid sample may include but is not limited to a structure that may include a plurality of walls that define a plurality of air gaps in the structure, wherein the plurality of walls may include a plurality of surfaces. The sensor may further include a hydrophobic clickable layer, wherein the hydrophobic clickable layer may be coated on the plurality of walls. The sensor may further include a binding material, wherein the binding material may be coated on the plurality of walls to bind to an analyte of interest. An initial surface energy of at least a portion of the plurality of surfaces of the plurality of walls may change when the analyte of interest binds with the binding material.

One or more of the following example features may be included. The structure may include at least one of a micrometer scaled structure and a nanometer scaled structure. At least one of the micrometer scaled structure and the nanometer scaled structure may include a reentrant structure. The hydrophobic clickable layer may include a hydrophobic component to enable wetting based sensing, wherein the hydrophobic clickable layer may further include clickable components to immobilize the binding material via a click chemistry reaction. The hydrophobic component and the clickable components may be co-immobilized on the plurality of walls via a coupling chemistry process. The coupling chemistry process may include a silane coupling agent. The coupling chemistry process may include a glutaraldehyde conjugation crosslinker. The coupling chemistry process may include an NHS-EDC carbodiimide crosslinking chemistry. The hydrophobic components may include one of alkanes, fats, fluorocarbons, and fluorinated molecules. The clickable components may include clickable groups of one of azide, alkyne, thiol, alkene, tetrazine, trans-cyclooctene, bicyclo[6.1.0]nonyne, Dibenzocyclooctyne, and Trans-Cyclooctene. The click chemistry reaction may occur in aqueous solution. The binding material may include a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials. The change of the initial surface energy of at least the portion of the plurality of surfaces of the plurality of walls may be visually detectable with an instrument. The change of the initial surface energy of at least the portion of the plurality of surfaces of the plurality of walls may be visually detectable with a naked eye. The sensor may further include a colorimetric reporter, wherein the change of the initial surface energy of at least the portion of the plurality of surfaces of the plurality of walls may be visually detectable with a color change.

In another example implementation, a method of manufacturing a sensor for detecting an analyte of interest in a fluid sample may include but is not limited to providing a structure that may include a plurality of walls that define a plurality of air gaps in the structure, wherein the plurality of walls may include a plurality of surfaces. The plurality of walls may be coated with a hydrophobic clickable layer. The plurality of walls may be coated with a binding material to bind to an analyte of interest. An initial surface energy of at least a portion of the plurality of surfaces of the plurality of walls may change when the analyte of interest binds with the binding material.

One or more of the following example features may be included. The structure may include at least one of a micrometer scaled structure and a nanometer scaled structure. At least one of the micrometer scaled structure and the nanometer scaled structure may include a reentrant structure. The hydrophobic clickable layer may include a hydrophobic component to enable wetting based sensing, wherein the hydrophobic clickable layer may further include clickable components to immobilize the binding material via a click chemistry reaction. The hydrophobic component and the clickable components may be co-immobilized on the plurality of walls via a coupling chemistry process. The coupling chemistry process may include a silane coupling agent. The coupling chemistry process may include a glutaraldehyde conjugation crosslinker. The coupling chemistry process may include an NHS-EDC carbodiimide crosslinking chemistry. The hydrophobic components may include one of alkanes, fats, fluorocarbons, and fluorinated molecules. The clickable components may include clickable groups of one of azide, alkyne, thiol, alkene, tetrazine, trans-cyclooctene, bicyclo[6.1.0]nonyne, Dibenzocyclooctyne, and Trans-Cyclooctene. The click chemistry reaction may occur in aqueous solution. The binding material may include a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials. The change of the initial surface energy of at least the portion of the plurality of surfaces of the plurality of walls may be visually detectable with an instrument. The change of the initial surface energy of at least the portion of the plurality of surfaces of the plurality of walls may be visually detectable with a naked eye. The sensor may further include a colorimetric reporter, wherein the change of the initial surface energy of at least the portion of the plurality of surfaces of the plurality of walls may be visually detectable with a color change. A colorimetric reporter may be provided, wherein the change of the initial surface energy of at least the portion of the plurality of surfaces of the plurality of walls is visually detectable with a color change via the colorimetric reporter.

In another example implementation, a method of detecting an analyte of interest may include but is not limited to contacting the sensor described throughout with a sample. An initial surface energy of at least a portion of the plurality of surfaces of the plurality of walls may change when the analyte of interest is present in the sample. A first mode may transition to a second mode based upon, at least in part, changing the initial surface energy.

In another example implementation, a sensor for detecting an analyte of interest in a sample may include but is not limited to a structural component grown on a surface from an initiator associated with a nucleic acid linker that is tethered to the surface, wherein a color of the surface may change upon growth of the structural component. The sensor may further include a surface associated with a ribonucleoprotein (RNP) complex that may include a CRISPR associated (Cas) nuclease, a guide RNA (gRNA) that may include a region that binds to the Cas nuclease, and a region that is complementary to a target nucleic acid sequence. When the target nucleic acid sequence contacts the gRNA, the gRNA may bind to the target nucleic acid sequence, the RNP complex may cleave the nucleic acid linker and may release the structural component grown on the surface, and may produce a detectable signal indicative of the target nucleic acid sequence being present.

One or more of the following example features may be included. The structural component may be a thin film. The structural component may be a patterned nanostructure and a nanoparticle. The initiator may be a polymerization initiator. The nucleic acid linker may be one of a single-stranded DNA (ssDNA), double-stranded DNA (dsDNA), and RNA. The target nucleic acid may be one of a single-stranded DNA (ssDNA), double-stranded DNA (dsDNA), and RNA. The Cas nuclease may be a type V Cas nuclease. The type V Cas nuclease may be one of Cas12a (Cpf1), Cas12b (C2c1), Cas12d, Cas12f (Cas14), and Cas12g. The Cas nuclease may be a type VI Cas nuclease. The type VI Cas nuclease may be one of Cas13a (C2c2), Cas13b, and Cas13d. The detectable signal may be visually detected by an instrument. The detectable signal may be visually detected by a naked eye. The detectable signal may be generated from destruction of at least a portion of a structural color indicator.

A method of detecting an analyte of interest may include but is not limited to contacting the sensor described throughout with a sample. When the analyte of interest is present in the sample, the nucleic acid linker may be cleaved, the structural component grown on the surface may be released, and a detectable signal indicative of the target nucleic acid sequence being present in the sample may be produced.

Generally, wetting based sensors typically require hydrophobic components to be immobilized on the sensor surface to enable an effective signal readout upon analyte binding; however, the hydrophobic components may require organic solvents to dissolve and process, which might not be compatible with the some molecular receptors that normally dissolve well only in aqueous solution. Therefore, as will be discussed in greater detail below, the present disclosure may co-immobilize hydrophobic components and molecular receptors on the sensor surface for precise control of wetting based sensing.

The present disclosure may relate to a device for the detection of analytes in a liquid sample. The device may utilize molecular receptors with high affinity for an analyte, such as metal ions, small molecules, proteins, or nucleic acids, that may selectively bind to said analyte and, upon binding, may lead to a visual indication of the presence of the analyte. Such a device may be used as a rapid, point-of-care molecular diagnostic to assist in the identification, assessment and treatment of various medical conditions for healthcare practitioners or individuals in clinical and non-clinical settings.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

The disclosure is based, in part, upon a unique colorimetric sensor that may detect an analyte of interest in a fluid or liquid sample. In a first aspect, the present disclosure relates to a colorimetric sensor that may detect an analyte of interest in a fluid sample. In some embodiments, the sensor may include a plurality of surfaces and a molecular receptor to receive an analyte of interest. Each surface may define a void and at least one surface may define a fluid inlet. In some implementations, the sensor may be configured such that, when an analyte contacts the molecular receptor and binds to such receptor, a wettability of at least one of the plurality of surfaces changes thereby to cause a detectable color change in the sensor. In some applications, the sensor may be configured such that, when the receptor receives the analyte, an amount of fluid present in the voids changes, thereby changing a refractive index of at least a portion of the sensor.

In some embodiments, one or more of the following may apply: a hydrophobic material may be coated on the plurality of surfaces; the sensor may include a solid structure that includes the plurality of surfaces; the molecular receptor may be organic or inorganic; the molecular receptor may be coated on one or more of the plurality of surfaces; the structure may be formed from the molecular receptor; the structure may include a dielectric material and/or a metallic material and/or semiconductor material and/or stack of dielectric/metallic/semiconductor or combination of any of these materials; and/or the structure may include an inverse opal photonic crystal or an inverse opal film; and/or the structure may include a straight micro/nanopillar structure; and/or the structure may include a reentrant structure such as but are not limited to inverted micro/nanocones, micro/nano hoodoo structures (or T-shape). The voids may also be formed in between the micro/nanopillars, or between the inverted micro/nanocones, or between the micro/nano hoodoo structures (or T-shape). Moreover, in some applications, one or more of the following may apply: each void may be substantially spherically shaped; each void may be substantially cylindrically shaped; at least some of the plurality of voids may be interconnected; the plurality of voids may be isolated from one another; the plurality of voids may have a periodic distribution; neighboring voids may be spaced apart by a distance between 1 nanometer and 10,000 micrometers; and/or neighboring voids may be spaced apart by a distance corresponding to a wavelength range of visible light.

In some embodiments, the sensor may also include metal positioned at a bottom of each cylindrically-shaped void and metal positioned outside a top of each cylindrically-shaped void. In some variations, the sensor may be disposed upon or integrated within a surface.

In a second aspect, the present disclosure relates to a method for detecting an analyte of interest in a fluid sample. In some embodiments, the method may include the process steps of (a) contacting a colorimetric sensor with the fluid sample and (b) detecting whether a color change occurs. A color change is indicative that the analyte is present in the fluid sample. In some implementations, the sensor may include a plurality of surfaces and a molecular receptor defining a cavity shaped to receive an analyte of interest. Each surface defines a void and at least one surface defines a fluid inlet. In some applications, the sensor may be configured such that, when an analyte contacts the molecular receptor and becomes bound to it, a wettability of at least one of the plurality of surfaces changes thereby to cause a detectable color change in the sensor. In some implementations, the sensor may be configured such that, when the receptor receives the analyte, an amount of fluid present in the voids changes, thereby changing a refractive index of at least a portion of the sensor.

The present disclosure, in some implementations, relates to a clickable hydrophobic coating on a micro/nano structure to maintain the affinity of the receptor while precisely controlling the wetting property of the surface. A hydrophobic molecule may be co-immobilized with a clickable molecule onto the above-mentioned sensor surface. In order to create a sensing surface utilizing the wetting control, a hydrophobic surface is generally needed. However, it is extremely difficult, if not impossible, to disperse or dissolve hydrophobic molecules in aqueous solution, so an organic solvent is typically required to dissolve the hydrophobic molecules. On the other hand, the receptor molecules, such as an aptamer, are not stable in organic solvents and an aqueous solution is always preferred. To overcome this example and non-limiting issue, a clickable molecule may be co-immobilized along with a hydrophobic molecule in organic solvent and then covalently bound to the receptor (e.g., via the click chemistry reaction) in aqueous solution.

The present disclosure also relates to a cleavable surface that may be produced from a precisely controlled surface-initiated polymerization process with DNA (or any nucleic acid) oligo initiator. A target-binding induced trans-cleavage of the non-target DNA oligo linkers assisted by CRISPR-cas12a protein complex cleaves the polymer grown on the surface and produces a visible color change by destructing the subwavelength nanostructure that generates the structural color. It will be appreciated that while DNA may be used in the description, any suitable nucleic acid may be used without departing from the scope of the present disclosure. As such, the use of DNA anywhere in the present disclosure should be taken as example only and not to otherwise limit the scope of the disclosure.

In general, in various example embodiments, the present disclosure relates to devices and methods for the detection of nucleic acid analytes in a fluid (e.g., liquid) sample. More specifically, the devices and methods in some example implementations, integrate a hydrophobic component and hydrophilic receptor (or vice versa) onto the sensor surface via a clickable surface to enable a wetting based sensing, and may provide a (e.g., optical) signal as a notification to an end user upon detection. In some implementations, the devices and methods may also integrate a cleavable surface that may be removed to exhibit a visually detectable signal upon detection of the analyte.

To provide an overall understanding of the disclosure, certain example embodiments will now be described, including devices, methods of making the devices, and methods of detecting an analyte target molecule of interest (e.g., in a fluid sample or otherwise). However, the devices and methods described herein may be adapted and modified as appropriate for the application being addressed and the devices and methods described herein may be employed in other suitable applications. For example, other suitable applications may include, but are not limited to, quantitative detection of an analyte, detection of subtle changes by using instruments, and detection of a gene variant. All such adaptations and modifications are to be considered within the scope of the disclosure.

Throughout the description, where compositions and devices such as a sensor are described as having, including, or comprising specific components, or where processes and methods are described as having, including, or comprising specific steps, it is contemplated that, additionally, there are compositions and devices of the present disclosure that consist essentially of, or consist of, the recited components, and that there are processes and methods according to the present disclosure that consist essentially of, or consist of, the recited processing steps. The terminology used herein is for the purpose of describing particular implementations only and is not intended to be limiting of the disclosure. As used herein, the singular forms “a”, “an” and “the” are intended to include the plural forms as well, unless the context clearly indicates otherwise. As used herein, the language “at least one of A and B” (and the like) as well as “at least one of A or B” (and the like) should be interpreted as covering only A, only B, or both A and B, unless the context clearly indicates otherwise. It will be further understood that the terms “comprises” and/or “comprising,” when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a device or a method described herein can be combined in a variety of ways without departing from the spirit and scope of the present disclosure, whether explicit or implicit herein. For example, where reference is made to a particular feature, that feature can be used in various embodiments of the devices of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without departing from the present teachings and disclosure. For example, it will be appreciated that all features described and depicted herein can be applicable to all aspects of the disclosure described and depicted herein.

The articles “a” and “an” are used in this disclosure to refer to one or more than one (i.e., to at least one) of the grammatical object of the article, unless the context is inappropriate. By way of example, “an element” means one element or more than one element.

The term “and/or” is used in this disclosure to mean either “and” or “or” unless indicated otherwise.

It should be understood that the expression “at least one of” includes individually each of the recited objects after the expression and the various combinations of two or more of the recited objects unless otherwise understood from the context and use. The expression “and/or” in connection with three or more recited objects should be understood to have the same meaning unless otherwise understood from the context.

The use of the term “include,” “includes,” “including,” “have,” “has,” “having,” “contain,” “contains,” or “containing,” including grammatical equivalents thereof, should be understood generally as open-ended and non-limiting, for example, not excluding additional unrecited elements or steps, unless otherwise specifically stated or understood from the context.

Where the use of the term “about” is before a quantitative value, the present disclosure also includes the specific quantitative value itself, unless specifically stated otherwise. As used herein, the term “about” refers to a ±10% variation from the nominal value unless otherwise indicated or inferred.

Where a percentage is provided with respect to an amount of a component or material in a composition such as a polymer, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remains operable. Moreover, two or more steps or actions can be conducted simultaneously.

At various places in the present specification, features may be disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or example language herein, for example, “such as” or “including,” are intended merely to better show the present disclosure and does not pose a limitation on the scope of the disclosure. Unless the context clearly indicates otherwise, no language in the specification should be construed as indicating any non-claimed element in any particular example as essential to the practice of the present disclosure.

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

A hydrophobic surface is generally needed for wetting based sensor. In order to coat the sensor surface with a hydrophobic component, hydrophobic molecules typically need to be dissolved in organic solvent due to the insolubility of such molecules in aqueous solution. A wetting based sensor (as discussed below) may also need to be coated with a molecular receptor to bind with the analyte of interest. The majority of molecular receptors (e.g., aptamers, antibodies, nucleic acids) are not soluble or stable in organic solvents, so an aqueous solution may be needed for immobilization of receptors on a sensor surface. Thus, the present disclosure may alleviate some or all of these disadvantages by providing a hydrophobic clickable surface that facilitates the co-immobilization of receptors and hydrophobic components for wetting based sensor construction.

The present disclosure may also provide a way to construct a cleavable surface as the functional component for a colorimetric or other type of visual sensor.

A wetting based sensor may be described as a sensor detecting wetting mode changes. The final readout or color change may be induced by the wetting mode change resulting from the introduction of the analyte. There are two different example wetting mode changes that are energetically favorable: from a Cassie mode to Wenzel mode transition, and from a slippery Wenzel mode to a sticky Wenzel mode. Both mode changes will be described in the following sections. There may be other example wetting mode changes that are not energetically favorable, for example, from Wenzel mode to Cassie mode transition, and from a sticky Wenzel mode to a slippery Wenzel mode. The following section describes the energetically favorable transitions only for the purpose of illustration and not limitation, although the non-energetically favorable mode changes may also be used without departing from the scope of the present disclosure.

Two wetting modes can exist when a fluid (e.g., liquid) interacts with a hydrophobic solid surface. Cassie mode is known to prevent fluid (e.g., liquid) from penetrating into air gaps, such as the air gaps between the pillars described throughout, by forming a solid-liquid-air interface, so that the liquid is extremely mobile (i.e., "non-sticky") and can roll freely on the solid surface using only gravity when the solid surface is tipped, tilted or flipped. Wenzel mode is another wetting mode in which the fluid (e.g., liquid) penetrates into the air gaps of a structured surface, such as the air gaps between the pillars, which enables the fluid (e.g., liquid) to fully wet the surface of the structure and become immobile (i.e., "sticky") on the solid surface. In the following text, "non-sticky" may be used as an interchangeable term with "slippery" to indicate a slippery state describing the mobile nature of a liquid on a designed surface when the surface is tilted or flipped, while "sticky" may be used interchangeably with "wet" to indicate a wet state of the liquid in which the liquid adheres to or is adsorbed by the solid surface, preventing the liquid from running off of the solid surface even when the surface is tilted or flipped. The physical origin of the "sticky" Wenzel mode is liquid pinning, which results from the interaction of liquid with the solid surface.

The in-flow and/or presence of a specific fluid, e.g., a fluid containing a target analyte of interest, in the air gaps/voids of a three-dimensional ("3D") structure (such as the pillars) may be used in diagnostic devices, e.g., photonic crystals, micropillar arrays, nanopillar arrays, multilayer dielectric stack, etc., and other visual-based (e.g., colorimetric) sensors, to verify or confirm the presence of the specific fluid (i.e., the analyte of interest in the fluid). Indeed, and more particularly, a color change detectable in the visible spectrum of light refracted by the structure due to, inter alia, a difference in the refractive index of the structure because of the presence of the fluid in the air gaps/voids may be used to identify the nature of the fluid captured in the air gaps of the structure. In this type of sensor device, the sensing mechanism is based on a Cassie-to-Wenzel transition. More specifically, the initial wetting state may be a Cassie mode that prevents liquid from infiltrating into air gaps/voids, while the end wetting state upon analyte binding may be a Wenzel mode that allows liquid to infiltrate the air gaps/voids and adhere to or be adsorbed by the surface due to the changing surface energy caused by the binding. The opposite may also be true (e.g., Wenzel-to-Cassie). In some implementations, when the sensor is not paired with a colorimetric reporter, the current mode may be sufficient to provide the indication of the presence of the analyte of interest (e.g., Cassie mode may indicate the presence or absence of the analyte of interest, whereas the Wenzel mode may indicate the opposite.

FIG. 1 shows a non-limiting example of micro/nanopillar sensor coated with binding materials. Examples of binding materials may include but are not limited to aptamers, antibodies, molecularly imprinted polymer (MIP), SOMAmers, affimers, DNA/RNA oligos, etc. The element 110 may be a pillar structure with a hydrophobic coating 120. The color indicator element may be, e.g., structural color, dye coating layer, any dielectric coating, dielectric/metal stacks, or combination of dielectric/metal/semiconductor materials. The binding material 130 (e.g., aptamer) in the example is properly folded and immobilized on the sensor surface via molecular interaction forces such as but not limited to covalent bond, hydrogen bond, electrostatic forces, Van der Waal forces, hydrophobic-hydrophobic forces, fluorous-affinity forces, etc. Without binding with analyte 140, the surface energy is strong enough to prevent infiltration of liquid the micro/nanopillar grooves (voids), as described with the Cassie mode. Once binding with analyte 140, the surface energy will change, leading to the infiltration of liquid into the micro/nanopillar grooves (as described with the Wenzel mode) and induces a color change of the materials that may result from the optical refractive index change (due to the liquid penetration) near the photonic structures or hydration of the dye materials, etc.

Referring still to FIG. 1, there is shown a sensor 100 with an example micropillar structure as a functional sensing area (e.g., element 110) to detect target DNA/RNA sequences. The cylindrical micropillars are used only as non-limiting examples only rather than limitation. Other shapes and sizes of pillars or other geometrical structures may be used for the same purpose, for example, microspheres, nanospheres, microparticles, nanoparticles, square shaped cylinders, pyramid shapes, other reentrant structures, reversed cone arrays, hole arrays, micro-scaled islands and/or nano-scaled islands configured with any other shapes or irregular shapes and/or an aggregation of these structures and/or combination thereof. The structures in the functional area may be made from a wide range of materials, for a non-limiting example, dielectric materials or metal including silica, titanium dioxide, hafnium oxide, polymer, plastic, PDMS, gold, silver, aluminum, copper, iron, and the like, and combinations thereof. Furthermore, these structures (e.g., microstructures and/or nanostructures) may be separated from each other to form a plurality of air gaps/voids. Air gaps and voids and grooves may be used interchangeably. The sizes are not limited to micrometer scales, and examples may range from 1 micrometer to 1000 micrometers, they can also be any smaller scale than 1 micrometer (e.g., nanometer scale as small as 0.1 nanometer) or larger scale than 1000 micrometers (e.g., millimeter scale as large as 10 millimeters). In some implementations, separation distances between (e.g., adjacent) microstructures and/or nanostructures may be as close as about 0.1 nanometers ("nm"). In some variations, the separation distance may be in the range from 0.1 nm to 10,000 microns. It has been discovered that in some implementations, the micropillar array acts not only as a signal transducer for the wetting mode-based sensing in the detection step but also works as a functional component to facilitate the lysis and extraction process when the appropriate size, shape, and interpillar spacing are selected. For a non-limiting example, the micropillar (e.g., element 110) may be a cylinder shape. Indeed, in addition to being cylindrical, the micropillar may be rectangular or of other shapes. Typical depths for micropillar may range between about one (1) nm and about one (1) centimeter, or between about 500 nm and about 1 millimeter, or between about 1 micrometer and about 100 micrometers (or various combinations thereof). Typical diameters for cylindrical micropillars may range between about one (1) nm and about one (1) centimeter, or between about 500 nm and about 1 millimeter, or between about 1 micrometer and about 100 micrometers (or various combinations thereof). Typical spacing between adjacent micropillars may range between about one (1) nm and about one (1) centimeter, or between about 500 nm and about 1 millimeter, or between about 1 micrometer and about 100 micrometers (or various combinations thereof).

In some implementations, a layer (e.g., a thin layer with a thickness from 0.1 nm to several hundred micrometers) of oxide coating 150 (e.g., silica, titanium dioxide, hafnium oxide, and the like, and combinations thereof) may be used as a color generator for colorimetric readout. The thin film oxide coating 150 may also be applied conformally to the micropillar structure.

In some implementations, an additional hydrophobic material coating 120 is used along with micropillar structure as the signal transducer to facilitate a target binding induced wettability change (or wetting state change) as a readout signal (wetting mode sensing will be described in the following sections).

In some implementations, binding materials, also referred to herein as receptors or molecular recognition receptors (for example, peptide, deoxyribonucleic acid (DNA), ribonucleic acid (RNA), peptide nucleic acid (PNA), oligonucleotides, molecularly-imprinted polymer (MIP) materials, aptamers, slow off-rate modified aptamers (SOMAmers), affirmers, antibodies, hormones, coordination complex, metal organic framework (MOF) materials, porous coordination polymer materials, and combination thereof) may be immobilized via physical adsorption or chemical bonding on the sensor surface to assist capturing the analyte of interest. In some implementations, receptors may consist of complementary sequences of target DNA/RNA either with part or the whole length of the target DNA/RNA sequence.

Both the hydrophobic coating and binding materials may be applied (e.g., conformally) to the contour of the micro-nano-structures. In order to create a sensing surface utilizing the wetting control, a hydrophobic surface is generally needed. However, hydrophobic molecules used to coat the surface are hydrophobic in nature and typically only dissolve well in organic solvents. On the other hand, most of the receptors (e.g., antibodies, aptamers, MIPs, etc.) used to bind the target are generally dissolved well only in aqueous solution. Therefore, it is difficult to coat the surface with both hydrophobic molecules and molecular receptors in solution phase. To overcome this limit, a clickable molecule may be co-immobilized along with a hydrophobic molecule in organic solvent, and then the receptor may be reacted with clickable molecules to form chemical bond and become immobilized on the surface via the click chemistry reaction in aqueous solution.

Figure 2:
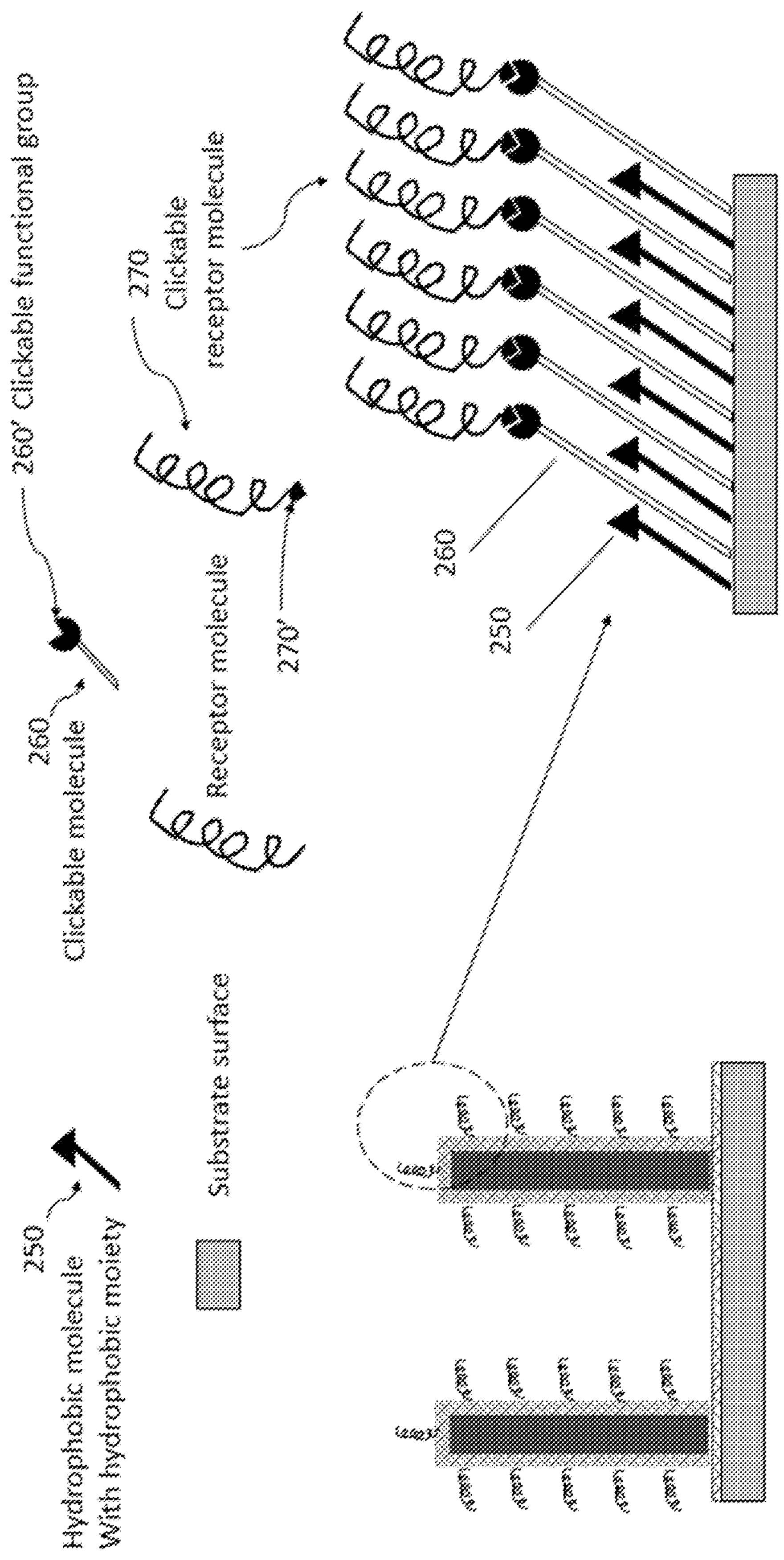
FIG. 2 shows an example co-immobilization process of a hydrophobic molecule and a clickable molecule used for further immobilization of a molecular receptor, in accordance with some embodiments of the present disclosure.

FIG. 2 shows a non-limiting example of co-immobilization of a hydrophobic molecule 250 along with clickable molecule 260 with clicking sites. The surface wetting property may be adjusted by tuning the surface coverage ratio between the hydrophobic molecule 250 and the clickable molecule 260 by adjusting their concentration or volume in solution. The hydrophobic molecules may include but are not limited to alkanes, fats, fluorocarbons, fluorinated molecules, and the like. The clickable molecules 260 may be molecules bearing a clickable functional group 260' that is able to form a carbon-heteroatom link (C-X-C) with another clickable functional group. For example, an azide functional group that is ready to react with an alkyne via copper-catalyzed azide-alkyne cycloaddition (CuAAC) reaction, strain-promoted alkyne-azide cycloaddition (SPAAC), or inverse electron-demand Diels-Alder (iEDDA) reaction. The receptor molecule 270 may contain another clickable functional group 270' that is ready to react with clickable functional group 260'. For example, an alkyne modified receptor molecule.

Figure 3:
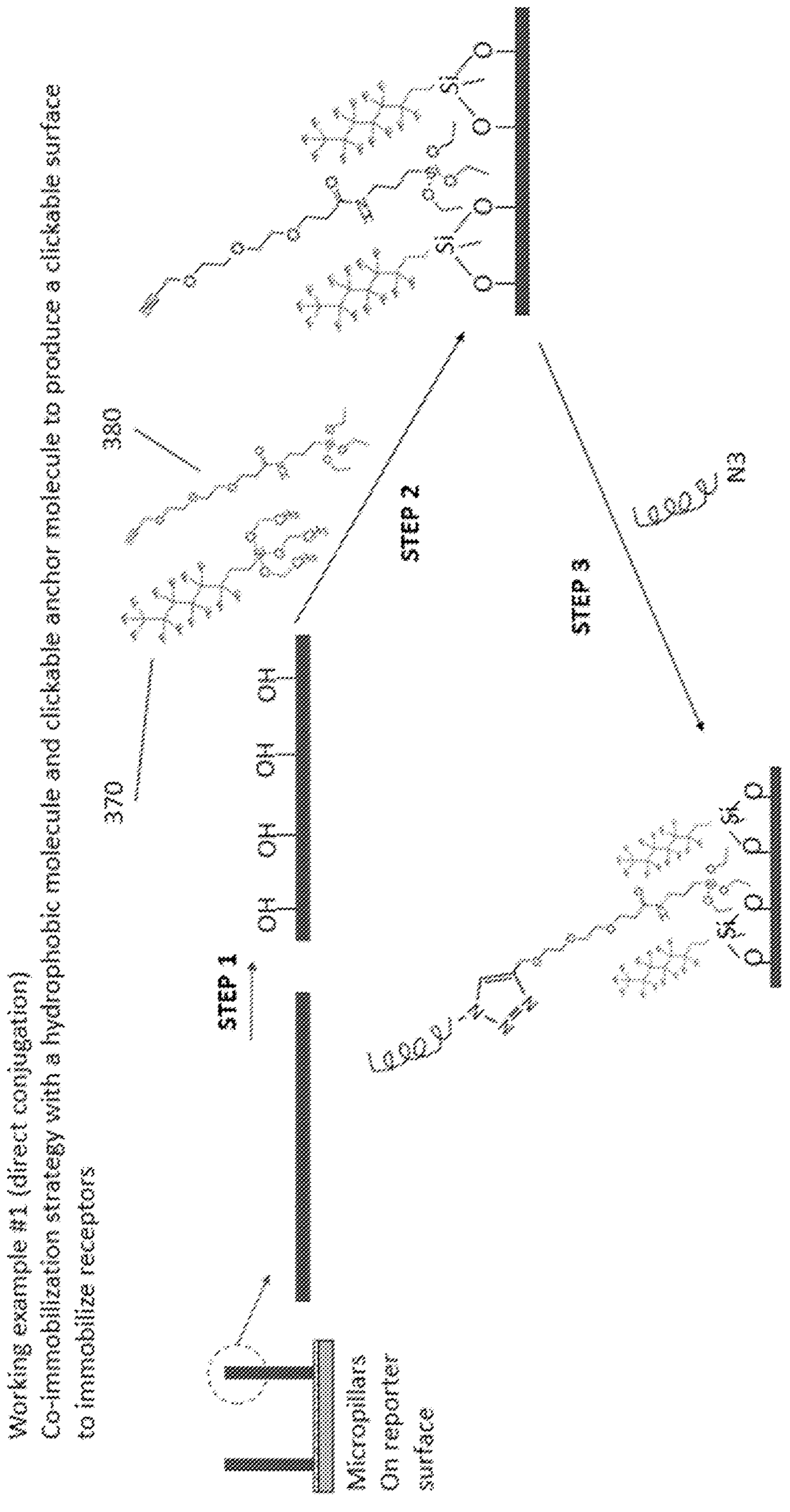
FIG. 3 shows a schematic of an example method of co-immobilization of a molecular receptor and hydrophobic molecule, to a sensor surface via silane chemistry, in accordance with some embodiments of the present disclosure.

FIG. 3 shows a non-limiting example of a direct conjugation of methoxysilane or ethoxysilane-based hydrophobic molecules 370 and clickable molecules 380 onto the sensor surface. Both solution phase and vapor phase deposition may be used as examples for desired ratio between these two molecules. Non-limiting examples of the hydrophobic molecules 370 may include fluorinated ethoxysilane and long alkyl chain bearing ethoxysilane. Non-limiting examples of fluorinated ethoxysilane molecules may include 1H,1H,2H,2H-Perfluorooctyltriethoxysilane, perfluorododecyl-1h,1h,2h,2h-triethoxysilane, and perfluorotetradecyl-1h,1h,2h,2h-triethoxysilane. Non-limiting examples of long alkyl chain bearing ethoxysilane molecules may include hexadecyltrimethoxysilane (HDTMS) and Octadecyltrimethoxysilane (ODTMS). A clickable component 380 is a clickable molecule that may include a clickable terminal group attached to the molecule. For non-limiting examples, these clickable groups include azide, alkyne, thiol, alkene, tetrazine, trans-cyclooctene, bicyclo[6.1.0]nonyne, Dibenzocyclooctyne, etc. FIG. 3 also depicts an example method for attaching oligos to the sensor surface via click chemistry reaction in three steps. For example, STEP 1 may include an activation process to produce a hydroxyl-rich surface. STEP 2 includes a vapor phase reaction (or other suitable reaction) to immobilize both an alkyne-bearing clickable silane molecule (e.g., Propargyl-PEG3-triethoxysilane) and a hydrophobic molecule (e.g., 1H,1H,2H,2H-Perfluorooctyltriethoxysilane) with the hydroxyl groups on the sensor surface to form a clickable surface. STEP 3 includes a copper catalyzed azide alkyne cycloaddition (CuAAC) click chemistry reaction between the alkyne-rich surface and an azide modified receptor (e.g., an aptamer oligo). The aptamer oligo is used as a non-limiting example. The azide modified oligo can be prepared using a standard oligo modification (e.g., from Integrated DNA Technologies). The concentration of azide modified oligos may be in the range from 1 femtoMolar to 1 milliMolar. In some applications, other click chemistry attachments may be used including, but not limited to, Strain promoted alkyne-azide cycloaddition (SPAAC), also referred to as the Cu-free click reaction, and the Inverse electron demand Diels-Alder (IEDDA) click reaction. For example, in a SPAAC reaction, the azide modified aptamers, prepared by standard oligo modification, may be immobilized to the sensor surface via the reaction between the azide group and a dibenzocyclooctyne (DBCO) functionalized sensor surface. The DBCO surface may be produced from the reaction between a DBCO-NHS ester with an amine-rich surface. Other type of receptors may be used, for example, peptide, deoxyribonucleic acid (DNA), ribonucleic acid (RNA), peptide nucleic acid (PNA), oligonucleotides, molecularly-imprinted polymer (MIP) materials, slow off-rate modified aptamers (SOMAmers), affirmers, antibodies, hormones, coordination complex, metal organic framework (MOF) materials, porous coordination polymer materials, and combination thereof. In some implementations, when other type of receptors are used, those receptors may be functionalized with clickable functional groups first and then react with the clickable surface. For example, antibodies may be functionalized by reacting with azide bearing amine reactive NHS ester, azide bearing carboxyl/carbonyl reactive NHS ester, DBCO bearing amine reactive NHS ester, DBCO bearing carboxyl/carbonyl reactive NHS ester, and the like.

Figure 4:
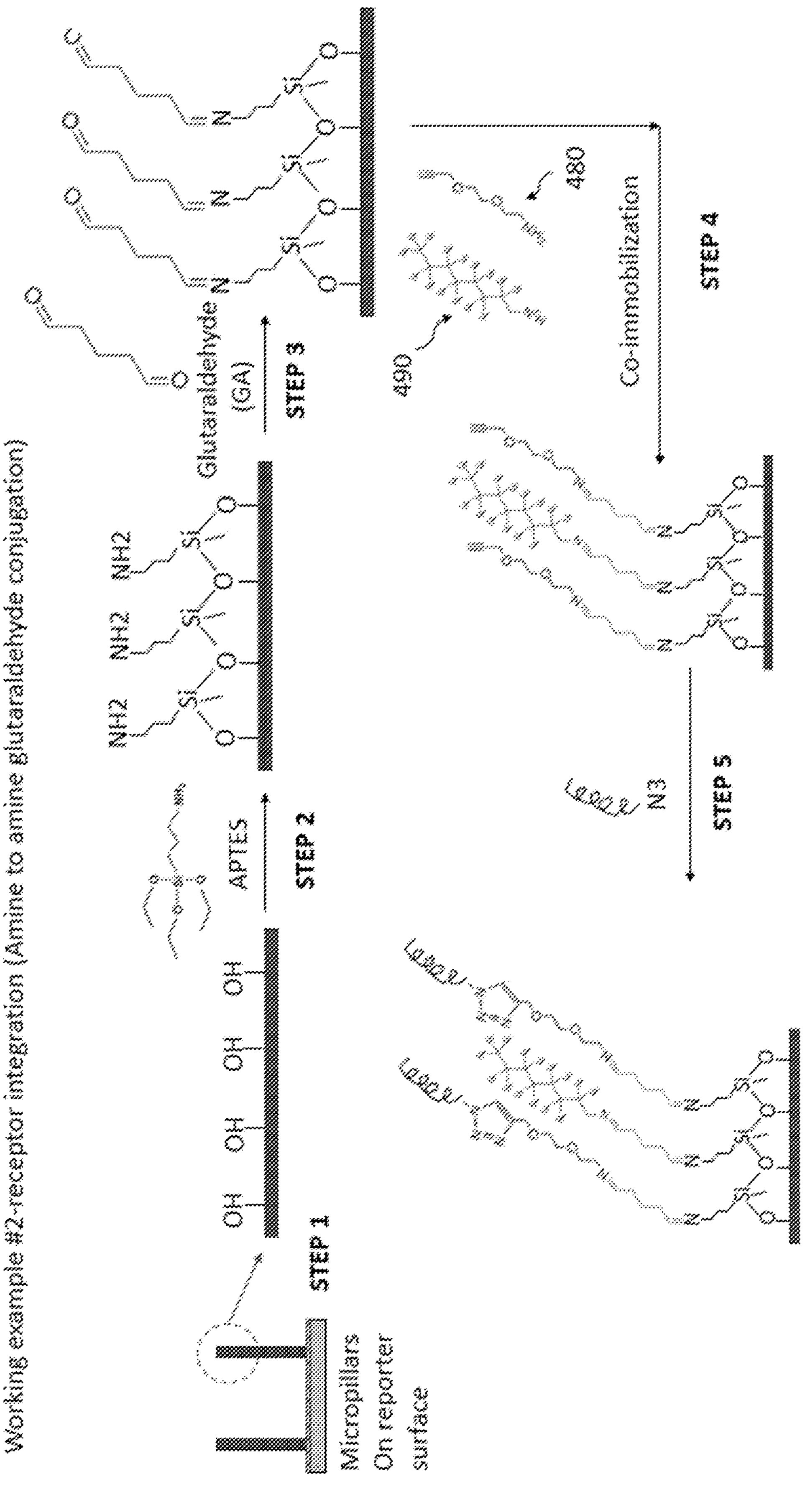
FIG. 4 shows a schematic of an example method of co-immobilization of a molecular receptor and hydrophobic molecule, to a sensor surface via glutaraldehyde crosslinking, in accordance with some embodiments of the present disclosure.

In some embodiments, such as the example shown in FIG. 4, there is a non-limiting example of stepwise conjugation of amine-bearing clickable molecules 480 and amine-bearing hydrophobic molecules 490 to aminated surface via amine-to-amine linker, for example glutaraldehyde. The primary amine bearing hydrophobic molecules 490 may include but are not limited to fluorinated and long alkyl chain primary amine compound, for example, 1H,1H-Perfluorooctylamine, Hexadecylamine, octadecylamine, etc. Clickable molecules may also be hydrophobic with a fluorinated moiety or with a long alkyl chain in the structure. The amine bearing clickable molecules 480 may include a clickable terminal group attached to the molecule. For non-limiting examples, these clickable groups may include azide, alkyne, thiol, alkene, tetrazine, trans-cyclooctene, bicyclo[6.1.0]nonyne, Dibenzocyclooctyne, Trans-Cyclooctene, etc. The aptamer oligo is used as a non-limiting example of receptor for example purposes only. The azide-bearing aptamer oligo may be conjugated to a surface via glutaraldehyde crosslinking in an example process, such as the process shown in FIG. 4. It will be appreciated after reading the present disclosure that these steps, as well as other steps described throughout, may be modified to achieve the desired result. STEP 1 may include an activation process to produce a hydroxyl-rich surface. The activation process may include, but is not limited to, an oxygen plasma treatment of the surface, a piranha solution mediated surface treatment, and the like. STEP 2 may include an amination process in which (3-Aminopropyl)triethoxysilane (APTES) is reacted with the hydroxyl-rich surface from STEP 1. This amination process may occur in either the solution phase or gaseous phase. For example, the amination may proceed at room temperature in a 2% APTES solution in toluene for one hour, or in APTES vapor phase within a sealed reactor at 150° C. Subsequently in STEP 3, the aminated surface may be reacted with one of the two carbonyl functional groups of a glutaraldehyde crosslinker to yield a carbonyl-rich surface. STEP 4 includes a vapor phase reaction to immobilize both an alkyne-bearing clickable silane molecule (e.g., Propargyl-PEG2-amine) and a hydrophobic molecule (e.g., 1H,1H-Perfluorooctylamine) with the carbonyl groups on the sensor surface to form a hydrophobic clickable surface. STEP 5 includes a copper catalyzed azide alkyne cycloaddition (CuAAC) click chemistry reaction between the alkyne-rich surface and an azide modified receptor (e.g., an aptamer oligo). The aptamer oligo is used as a non-limiting example only. The azide modified oligo can be prepared using a standard oligo modification (e.g., from Integrated DNA Technologies). The concentration of azide modified oligos may be in the range from 1 femtoMolar to 1 milliMolar. In some applications, other click chemistry attachments may be used including, but not limited to, Strain promoted alkyne-azide cycloaddition (SPAAC), also referred to as the Cu-free click reaction, and the Inverse electron demand Diels-Alder (IEDDA) click reaction. For example, in a SPAAC reaction, the azide modified aptamers, prepared by standard oligo modification, may be immobilized to the sensor surface via the reaction between the azide group and a dibenzocyclooctyne (DBCO) functionalized sensor surface. The DBCO surface may be produced from the reaction between a DBCO-NHS ester (e.g., DBCO-PEG4-NHS Ester) with an amine-rich surface. Other type of receptors may be used, for example, peptide, deoxyribonucleic acid (DNA), ribonucleic acid (RNA), peptide nucleic acid (PNA), oligonucleotides, molecularly-imprinted polymer (MIP) materials, slow off-rate modified aptamers (SOMAmers), affirmers, antibodies, hormones, coordination complex, metal organic framework (MOF) materials, porous coordination polymer materials, and combination thereof. When other type of receptors are used, those receptors may be functionalized with clickable functional groups first and then react with the clickable surface. For example, antibodies may be functionalized by reacting with azide bearing amine reactive NHS ester, azide bearing carboxyl/carbonyl reactive NHS ester, DBCO bearing amine reactive NHS ester, DBCO bearing carboxyl/carbonyl reactive NHS ester, and the like.

Figure 5:
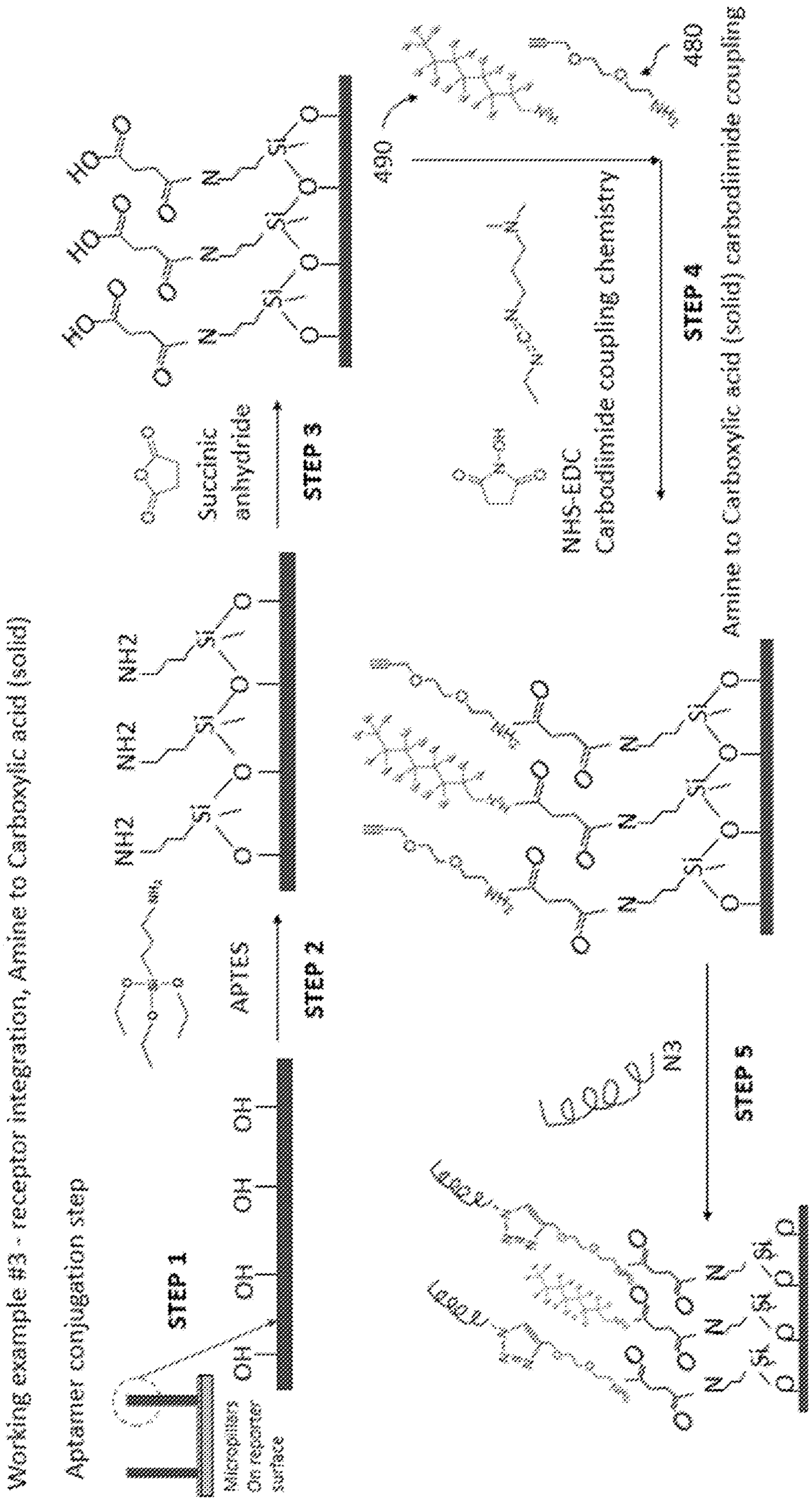
FIG. 5 shows a schematic of an example method of co-immobilization of a molecular receptor and hydrophobic molecule, to a sensor surface by reacting primary amines to a carboxylic surface, in accordance with some embodiments of the present disclosure.

FIG. 5 depicts a non-limiting example of stepwise conjugation of amine-bearing clickable molecules 480 and amine-bearing hydrophobic molecules 490 to carboxylic acid-bearing surface via amine-to-carboxylic-acid linker. A non-limiting example of this conjugation may be NHS-EDC carbodiimide crosslinking chemistry. The primary amine-bearing hydrophobic molecules 490 and the amine-bearing clickable molecules 480 may include other similar functional groups as described in FIG. 4. For non-limiting examples, these clickable groups may include azide, alkyne, thiol, alkene, tetrazine, trans-cyclooctene, bicyclo[6.1.0]nonyne, Dibenzocyclooctyne, Trans-Cyclooctene, etc. The aptamer oligo is used as a non-limiting example of receptor for illustration purpose. The azide-bearing aptamer oligo may be conjugated to a surface via carbodiimide crosslinking chemistry in an example process, such as the process shown in FIG. 5. It will be appreciated after reading the present disclosure that these steps, as well as other steps described throughout, may be modified to achieve the desired result. STEP 1 may include an activation process to produce a hydroxyl-rich surface. The activation process may include, but is not limited to, an oxygen plasma treatment of the surface, a piranha solution mediated surface treatment, and the like. STEP 2 may include an amination process in which (3-Aminopropyl)triethoxysilane (APTES) is reacted with the hydroxyl-rich surface from STEP 1 to generate an amine-rich surface. This amination process may occur in either the solution phase or gaseous phase. For example, the amination may proceed at room temperature in a 2% APTES solution in toluene for one hour, or in APTES vapor phase within a sealed reactor at 150° C. Subsequently in STEP 3 the amine-rich surface may be converted into a carboxylic-rich surface via a ring opening amidation reaction of succinic anhydride with the primary amine groups on the sensor surface at room temperature. STEP 4 includes an amine to carboxylic acid carbodiimide coupling reaction in solution (or vapor) phase or EDC/NHS (1-Ethyl-3-[3-dimethylaminopropyl]carbodiimide hydrochloride/N-hydroxysuccinimide) coupling chemistry reaction to immobilize both an alkyne-bearing clickable molecule (e.g., Propargyl-PEG2-amine) and a hydrophobic molecule (e.g., 1H,1H-Perfluorooctylamine) with the carboxylic acid groups on the sensor surface to form a hydrophobic clickable surface. In some variations, an EDC/sulfo-NHS reaction may be used to prepare the hydrophobic clickable surface.

STEP 5 includes a copper catalyzed azide alkyne cycloaddition (CuAAC) click chemistry reaction between the alkyne-rich surface and an azide modified receptor (e.g., an aptamer oligo). The aptamer oligo is used as a non-limiting example. The azide modified oligo can be prepared using a standard oligo modification (e.g., from Integrated DNA Technologies). The concentration of azide modified oligos may be in the range from 1 femtoMolar to 1 milliMolar. In some applications, other click chemistry attachments may be used including, but not limited to, Strain promoted alkyne-azide cycloaddition (SPAAC), also referred to as the Cu-free click reaction, and the Inverse electron demand Diels-Alder (IEDDA) click reaction. For example, in a SPAAC reaction, the azide modified aptamers, prepared by standard oligo modification, may be immobilized to the sensor surface via the reaction between the azide group and a dibenzocyclooctyne (DBCO) functionalized sensor surface. The DBCO surface may be produced from the reaction between a carboxyl reactive DBCO based amine molecule (e.g., DBCO-PEG4-amine) with a carboxyl-rich surface. Other type of receptors may be used, for example, peptide, deoxyribonucleic acid (DNA), ribonucleic acid (RNA), peptide nucleic acid (PNA), oligonucleotides, molecularly-imprinted polymer (MIP) materials, slow off-rate modified aptamers (SOMAmers), affirmers, antibodies, hormones, coordination complex, metal organic framework (MOF) materials, porous coordination polymer materials, and combination thereof. When other type of receptors are used, those receptors may be functionalized with clickable functional groups first and then react with the clickable surface. For example, antibodies may be functionalized by reacting with azide bearing amine reactive NHS ester, azide bearing carboxyl/carbonyl reactive NHS ester, DBCO bearing amine reactive NHS ester, DBCO bearing carboxyl/carbonyl reactive NHS ester, and the like. It will be understood after reading the present disclosure that other click chemistry techniques may also be used without departing from the scope of the present disclosure.

Figure 6:
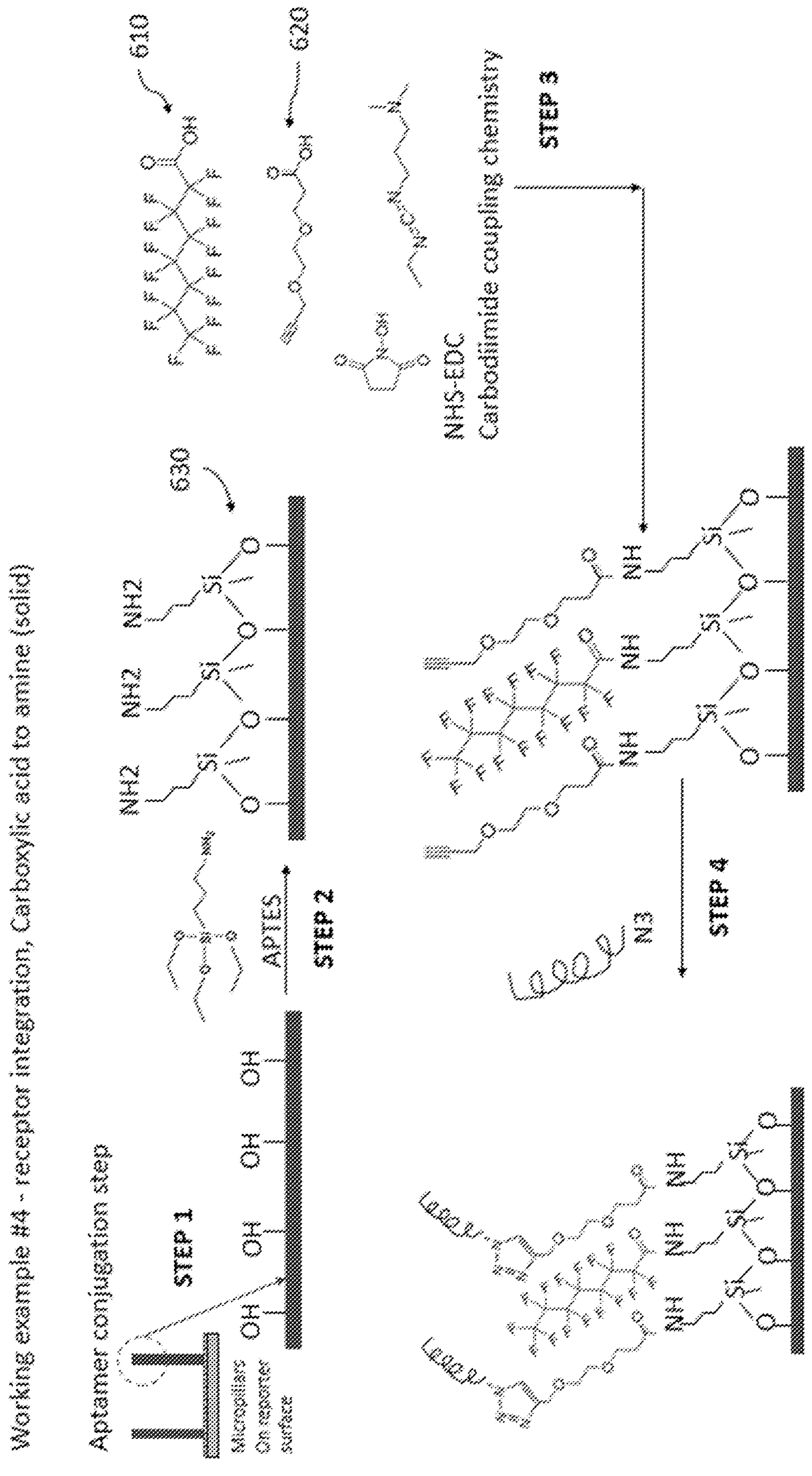
FIG. 6 shows a schematic of an example method of co-immobilization of a molecular receptor and hydrophobic molecule, to a sensor surface by reacting carboxylic groups to an amine-rich surface, in accordance with some embodiments of the present disclosure.

FIG. 6 demonstrates another non-limiting example of stepwise conjugation of carboxylic acid bearing hydrophobic molecules 610 and carboxylic acid bearing clickable molecules 620 to primary amine bearing sensor surface 630 via amine-to-carboxylic-acid linker. A non-limiting example of this conjugation may be NHS-EDC carbodiimide cross-linking chemistry. The carboxylic acid bearing hydrophobic molecules may include but are not limited to fluorinated and long alkyl chain carboxylic acid compound, saturated and unsaturated fatty acid, for example, Perfluorononanoic acid, Stearic acid, Arachidic acid, etc. Clickable molecules may also be hydrophobic with a fluorinated moiety or with a long alkyl chain in the structure. The carboxylic acid bearing clickable molecules may include a clickable terminal group attached to the molecule, for non-limiting example, these clickable groups include azide, alkyne, thiol, alkene, tetrazine, trans-cyclooctene, bicyclo[6.1.0]nonyne, Dibenzocyclooctyne, Trans-Cyclooctene, etc. The aptamer oligo is used as a non-limiting example of receptor for illustration purpose. The azide-bearing aptamer oligo may be conjugated to a surface via carbodiimide crosslinking chemistry in a 4-step process. It will be appreciated after reading the present disclosure that these steps, as well as other steps described throughout, may be modified to achieve the desired result. STEP 1 may include an activation process to produce a hydroxyl-rich surface. The activation process may include, but is not limited to, an oxygen plasma treatment of the surface, a piranha solution mediated surface treatment, and the like. STEP 2 may include an amination process in which (3-Aminopropyl)triethoxysilane (APTES) is reacted with the hydroxyl-rich surface from STEP 1 to generate an amine-rich surface. This amination process may occur in either the solution phase or gaseous phase. For example, the amination may proceed at room temperature in a 2% APTES solution in toluene for one hour, or in APTES vapor phase within a sealed reactor at 150° C. STEP 3 includes an carboxylic acid to amine carbodiimide coupling reaction in solution (or vapor) phase or EDC/NHS (1-Ethyl-3-[3-dimethylaminopropyl]carbodiimide hydrochloride/N-hydroxysuccinimide) coupling chemistry reaction to immobilize both an alkyne-bearing clickable molecule (e.g., Propargyl-PEG2-acid) and a hydrophobic molecule (e.g., Perfluorononanoic acid) with the primary amine groups on the sensor surface to form a hydrophobic clickable surface. In some variations, an EDC/sulfo-NHS reaction may be used to prepare the hydrophobic clickable surface. STEP 5 includes a copper catalyzed azide alkyne cycloaddition (CuAAC) click chemistry reaction between the alkyne-rich surface and an azide modified receptor (e.g., an aptamer oligo) as described above. The aptamer oligo is used as a non-limiting example. The azide modified oligo can be prepared using a standard oligo modification (e.g., from Integrated DNA Technologies). The concentration of azide modified oligos may be in the range from 1 femtoMolar to 1 milliMolar. In some applications, other click chemistry attachments may be used including, but not limited to, Strain promoted alkyne-azide cycloaddition (SPAAC), also referred to as the Cu-free click reaction, and the Inverse electron demand Diels-Alder (IEDDA) click reaction. For example, in a SPAAC reaction, the azide modified aptamers, prepared by standard oligo modification, may be immobilized to the sensor surface via the reaction between the azide group and a dibenzocyclooctyne (DBCO) functionalized sensor surface. The DBCO surface may be produced from the reaction between an amine reactive DBCO based carboxylic acid molecule (e.g., DBCO-PEG4-acid) with an amine-rich surface 630. Other type of receptors may be used, for example, peptide, deoxyribonucleic acid (DNA), ribonucleic acid (RNA), peptide nucleic acid (PNA), oligonucleotides, molecularly-imprinted polymer (MIP) materials, slow off-rate modified aptamers (SOMAmers), affirmers, antibodies, hormones, coordination complex, metal organic framework (MOF) materials, porous coordination polymer materials, and combination thereof. When other type of receptors are used, those receptors may be functionalized with clickable functional groups first and then react with the clickable surface.

For example, antibodies may be functionalized by reacting with azide bearing amine reactive NHS ester, azide bearing carboxyl/carbonyl reactive NHS ester, DBCO bearing amine reactive NHS ester, DBCO bearing carboxyl/carbonyl reactive NHS ester, and the like.

Figure 7:
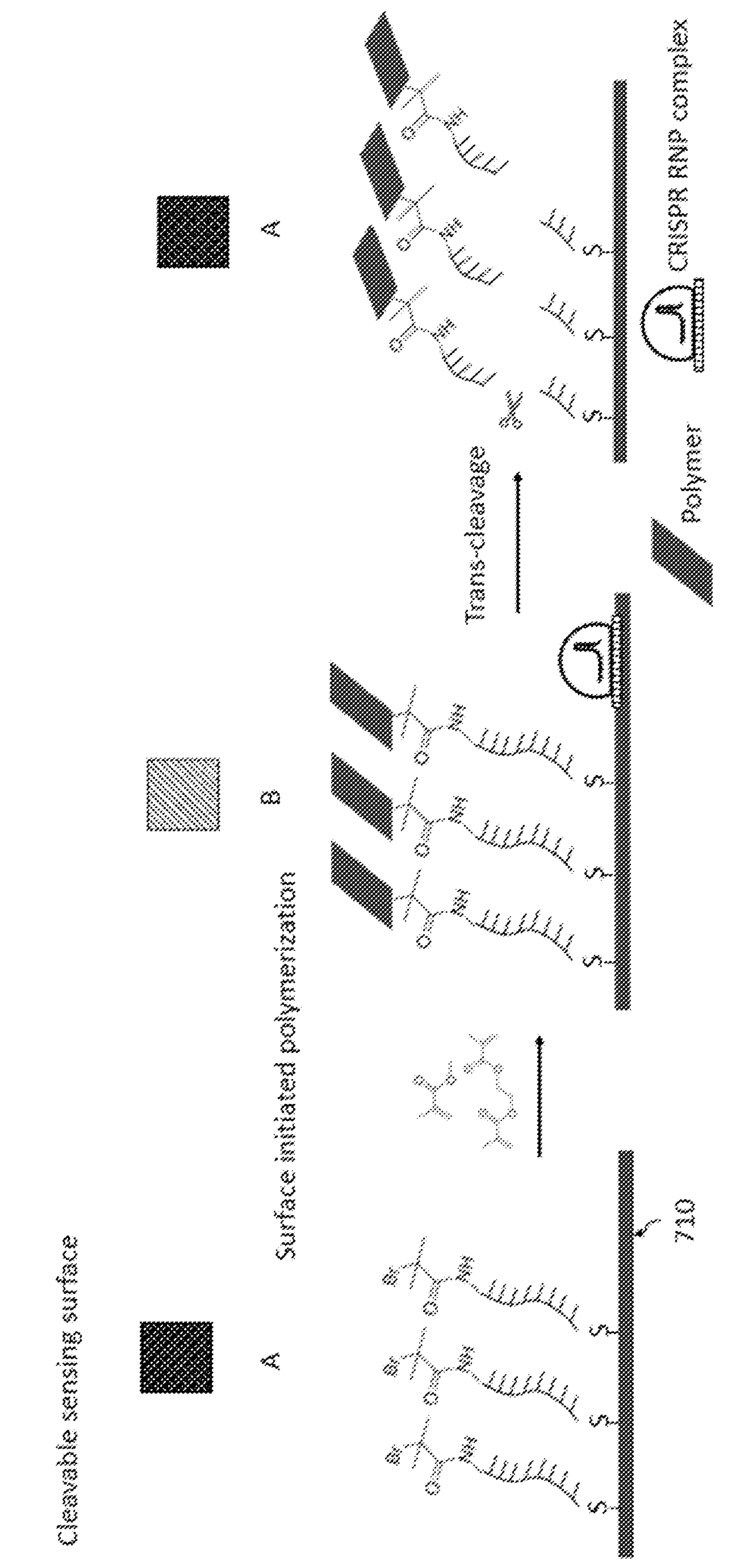
FIG. 7 shows an example of a cleavable sensor structure with DNA linker and integrated CRISPR functional components for target binding in accordance with some embodiments of the present disclosure.

In some implementations, a sensor may be constructed by a color change due to destruction of structural color component upon analyte binding. For instance, an example cleavable surface for colorimetric sensing is shown as a non-limiting example of such a sensor in FIG. 7. Nucleic acid linkers (e.g., single-stranded DNA (ssDNA), double-stranded DNA (dsDNA), or RNA) may be covalently (or otherwise) linked to an initiator (e.g., a polymerization initiator) and then immobilized on the solid surface 710. As a non-limiting example, the solid surface may be a structural color surface made from the thin film (e.g., dielectric, metal, or semiconductor) interference layer being constructed from continuous thin film stacks where each thin film is a structural component or a structural color surface produced from plasmonic resonance effect, photonic crystal effect, or some other color generation methodology where discontinuous thin films are used. To facilitate description, a thin film based structural color is used as a non-limiting example of a colorimetric reporter. In such a case, the structural color exhibited by the sensor is generated from the interaction between the (e.g., silica) thin film layer deposited on the silicon substrate and the polymer layer grown on the silica surface. A different color may be developed from the surface-initiated polymerization as a result of the thickness change on the sensor surface as shown in FIG. 7. The chip exhibits an initial color (e.g., color A on the sensor) but changes to a different color (e.g., color B on the sensor) after surface-initiated polymerization on the sensor surface. Then after the sensor chip is exposed to the analyte of interest (for example a nucleic acid), a target specific ribonucleoprotein (RNP) complex with CRISPR nuclease protein (for a non-limiting example, CRISPR-cas9) and guide RNA (gRNA) may be immobilized on the same surface and may be activated upon binding of the specific analyte target to enable non-specific cleaving. In certain embodiments, the Cas nuclease is a type V Cas nuclease, for example, a Cas12a (Cpf1), Cas12b (C2c1), Cas12d, Cas12f (Cas14), or Cas12g nuclease. In certain embodiments, the Cas nuclease is a type VI Cas nuclease, for example, a Cas13a (C2c2), Cas13b, or Cas13d nuclease. The specific analyte target may be a single-stranded DNA (ssDNA), double-stranded DNA (dsDNA), or RNA. The activated RNP cleaves the (e.g., DNA) oligo linkers and a color change can be expected due to the destroying of the structural color by decoupling the structural components that make the structural color. Then the color may be restored to the initial color (e.g., color A). The surface-initiated polymerization may be but not limited to an atom transfer radical polymerization (ATRP), a Reversible addition-fragmentation chain transfer (RAFT), Nitroxide-mediated radical polymerization (NMP), etc.

In some embodiments, the reporters described above are bound to a sensor surface by a nucleic acid (e.g., DNA) linker via thiol-gold interaction. In the thin-film based structural color system, a thin layer of gold may be deposited on the surface of the sensor to facilitate the immobilization of DNA linkers as shown in FIG. 7. For example, a DNA linker with its 5' end modified with thiol and 3' end modified with primary amine. A polymerization initiator may be covalently (or otherwise) linked to the DNA linker. For example, α-Bromoisobutyryl bromide (BIBB) initiator for ATRP polymerization may be reacting with the primary amine on the 3' end of the DNA linker. Then an ATRP reaction may be initiated to generate a thin layer of polymer film as one of the structural components on top of the sensor surface to generate the structural color. In some embodiments, the DNA linker may be co-immobilized with another hydrophobic component onto the sensor surface to enable wetting based sensing. Cleavage of the nucleic acid (e.g., DNA) linker results in a structural destruction of the reporter system, thereby causing an observable property change in the sensor. The observable property change may result from, for example, a surface energy change in a portion of the sensor, a wetting behavior change, or another physical property change (e.g., destruction of at least a portion of a structural color indicator). As a result of the property change, a portion of the sensor may change color or may suffer a color degradation or there may be a change in (or loss of) a monitored electrical signal, an optical signal, or the like by an instrument. In general, any sensor that undergoes any observable property change (e.g., by an instrument or by using the naked eye) as a result of reporter system destruction is within the scope of the invention. A non-limiting example embodiment of such a sensor is described below.

Figure 8:
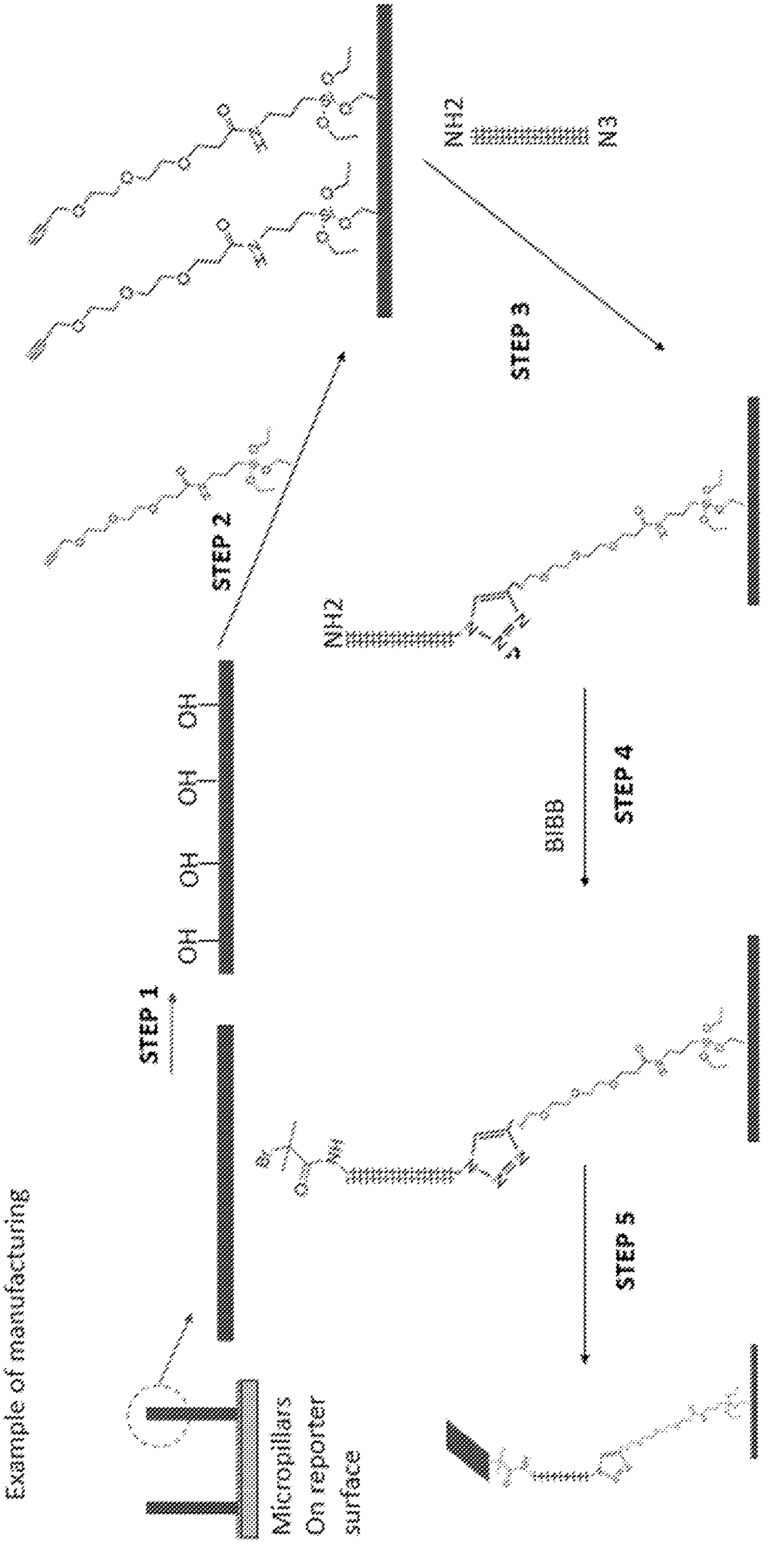
FIG. 8 shows a schematic of an example method of surface-initiated polymerization from a nucleic acid linker to generate a thin-film based colorimetric reporter, in accordance with some embodiments of the present disclosure.

FIG. 8 depicts immobilization method of DNA based initiator to the sensor surface via click chemistry reaction. It will be appreciated after reading the present disclosure that these steps, as well as other steps described throughout, may be modified to achieve the desired result. STEP 1 may include an activation process to produce a hydroxyl-rich surface. The activation process may include, but is not limited to, an oxygen plasma treatment of the surface, a piranha solution mediated surface treatment, and the like. STEP 2 includes a vapor (or solution) phase reaction to immobilize an alkyne-bearing clickable silane molecule (e.g., Propargyl-PEG3-triethoxysilane) with the hydroxyl groups on the sensor surface. STEP 2 may also include a co-immobilization of an alkyne-bearing clickable silane molecule and a hydrophobic molecule onto the hydroxyl-rich sensor surface. STEP 3 includes a copper catalyzed azide alkyne cycloaddition (CuAAC) click chemistry reaction between the alkyne-rich surface and an azide modified nucleic acid linker (e.g., a 5' end modified DNA or RNA). The nucleic acid linker may be modified with another amine at its 3' end. The primary amine group may facilitate the reaction with an ATRP initiator (e.g., BIBB) in STEP 4 to immobilize the initiator to the DNA linker. Then in STEP5, an ATRP polymerization may produce polymer brushes or crosslinked polymer brushes onto the surface to generate a color that is visually different from its original color prior to the polymerization. The DNA oligo is used as a non-limiting example. The azide and amine modified DNA linker can be prepared using a standard oligo modification (e.g., from Integrated DNA Technologies). The cleavable surfaces may be used along with an immobilized CRISPR protein (e.g., CRISPR cas9) or CRISPR protein solution to detect analyte of interest via a visually detectable color change as described above.

Figure 9B:
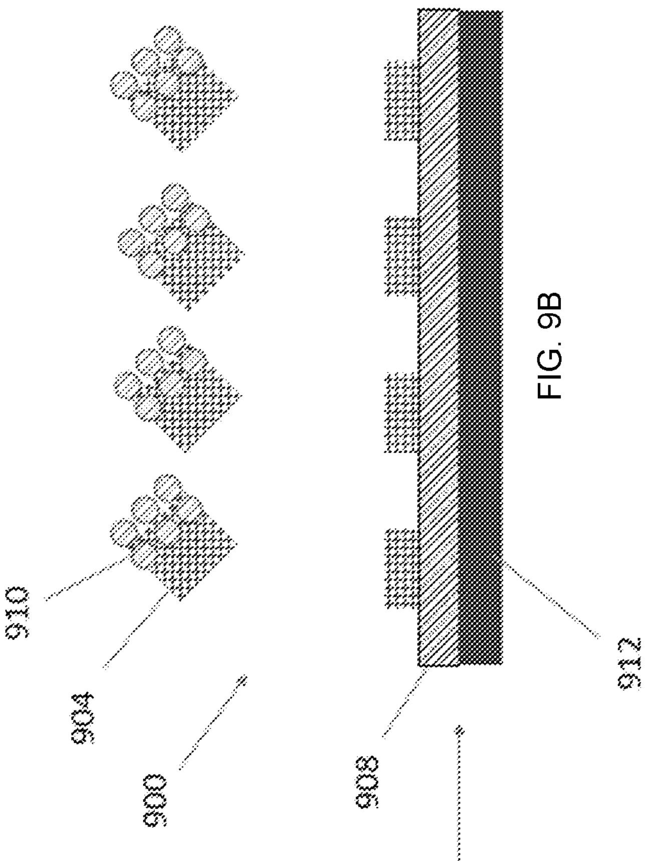
FIG. 9B depicts the structural color sensor of FIG. 9A, in which the DNA linkers have been cleaved.
Figure 9A:
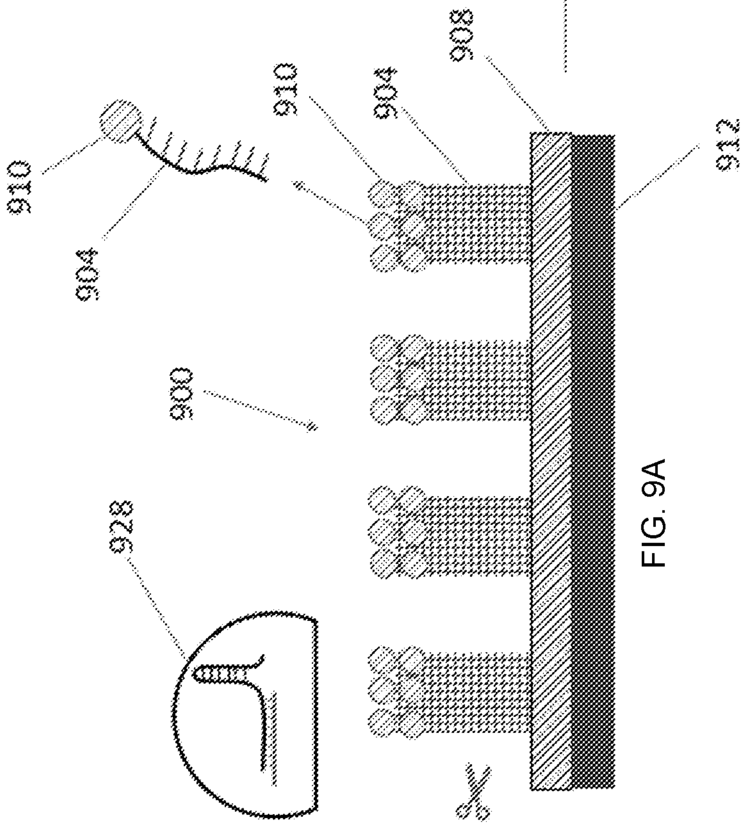
FIG. 9A depicts a structural color sensor, in accordance with one embodiment of the invention.

In some embodiments, nanometer sized structure may be used as the structural color generation technique. FIGS. 9A and 9B depict another embodiment of a structural color sensor (or indicator) 900, in particular a surface plasmon resonance-type colorimetric sensor 900 generated from patterned nanometer scaled structures. In the example, the sensor 900 includes a first layer of metal 908 (e.g., platinum, gold, silver, aluminum, copper, tungsten, and combinations thereof) deposited on an upper surface of a substrate 912. The sensor 900 also includes an array of DNA linkers 904 conjugated with a metal (or sometimes latex or other type of) nanoparticle 910, which is one of the compositional structural components that make the structural color. Non-limiting examples of such nanoparticles 910 include gold nanoparticles, polystyrene nanoparticles, CdSe quantum dots, carbon nanoparticles, or combinations of these nanoparticles, or conjugates of these nanoparticles with dye/pigment.

To ease of explanation, a metal nanoparticle 910 is used as a non-limiting example. In such a case, the structural color exhibited by the sensor 900 depicted in FIG. 9A is generated from the interaction of the metal nanoparticles 910 with the thin film of metal 908 underneath the patterned DNA linkers 904. More particularly, the scattered, reflected, or transmitted color is determined, e.g., primarily or at least in part, by a localized plasmon resonance between the two metal surfaces 908, 910 that are separated by a coupling distance (e.g., by the height of each DNA linker 904). The size and shape of the metal surfaces 908, 910 affect the plasmon resonance. Periodicity between adjacent metal surfaces (e.g., between top surfaces of adjacent DNA linkers 904, where the nanoparticles 910 are located) also affects the plasmon resonance. For example, the closer the metallic surface 908 is to the metallic surfaces 910, the greater the coupling between the interacting dipoles of the two metallic surfaces 908, 910. The greater the interactive dipole coupling, the greater the increase of the plasmon resonant wavelength. In contrast, the more distant the metallic surfaces 908, 910 are from one another, the weaker the coupling between the interacting dipoles, resulting in a decrease of the plasmon resonant wavelength. Moreover, the structural color generated by the sensor 900 depicted in FIG. 9A may either be the extinction (small metal particles) or scattering (large metal particles) from individual particles (e.g., Mie extinction or scattering), where "small" generally indicates a size range of the metal nanoparticles 910 from 0.001 nm to 30 nm and "large" generally indicates a size range of the metal nanoparticles 910 from 30 nm to 2 micrometers.

As shown in FIG. 9B, when a fluid sample containing a target analyte of interest is introduced to the sensor 900 and the RNP complex 928 (from FIG. 9A) is activated by a target nucleic acid sequence, the RNP complex 928 may non-specifically (or specifically) cleave the DNA linkers 904, thereby decoupling a top portion of the DNA linker 904 (including the conjugated metal nanoparticle 910) from the remaining portion of the sensor 900 (including the first layer of metal 908). The decoupling of the metal nanoparticle 910 from the first metal layer 908 results in a degradation of the color exhibited by the sensor 900 (e.g., a return from a first color exhibited by the sensor 900 prior to the decoupling to the color of the first layer of metal 908), thereby indicating the presence of the target analyte of interest in the fluid sample.

In one example method of manufacturing the surface plasmon resonance-type colorimetric sensor 900, a thin layer (e.g., of about 0.1 nm to several hundred nanometers) of metal 908 (e.g., platinum, gold, silver, aluminium, copper, tungsten, combinations thereof, and the like) may be applied to a top surface of the base substrate 912 (e.g., by metal deposition, chemical vapor deposition (CVD), sputtering, three-dimensional nanoprinting, plasma-enhanced chemical vapor deposition (PECVD), physical vapor deposition (PVD), electroless plating, and so forth). An array of DNA (or more general nucleic acid) linkers 904 may then be produced from, e.g., a surface-initiated polymerization (SIP) or surface-initiated hybridization chain reaction. Metal nanoparticles 910 conjugated with complementary ssDNA may be grafted to the array of DNA pillars 904. In some implementations, the initial patterned surface may be made from a variety of processes, including but not limited to electron beam chemical lithography (EBCL), soft lithography, surface initiated ATRP and RAFT polymerization. In some implementations, DNA molecules may be co-polymerized or functionalized with polymer brushes via click chemistry reaction. In some other implementations, DNA molecules may be co-immobilized with hydrophobic molecules onto the sensor surface. For a non-limiting example, polymer brushes with amine pendant groups (or other groups) may be employed for a reaction with a carboxylic acid group (or other group) on the biotin modified DNA molecules.

Clause 1. A sensor for detecting an analyte of interest in a fluid sample, the sensor comprising:

a structure including a plurality of walls that define a plurality of air gaps in the structure, wherein the plurality of walls include a plurality of surfaces;

a hydrophobic clickable layer, wherein the hydrophobic clickable layer is coated on the plurality of walls;

a binding material, wherein the binding material is coated on the plurality of walls to bind to an analyte of interest; and wherein an initial surface energy of at least a portion of the plurality of surfaces of the plurality of walls changes when the analyte of interest binds with the binding material.

Clause 2. The sensor of Clause 1, wherein the structure includes at least one of a micrometer scaled structure and a nanometer scaled structure.

Clause 3. The sensor of Clause 2, wherein at least one of the micrometer scaled structure and the nanometer scaled structure includes a reentrant structure.

Clause 4. The sensor of Clause 1, wherein the hydrophobic clickable layer includes a hydrophobic component to enable wetting based sensing, wherein the hydrophobic clickable layer further includes clickable components to immobilize the binding material via a click chemistry reaction.

Clause 5. The sensor of Clause 4, wherein the hydrophobic component and the clickable components are co-immobilized on the plurality of walls via a coupling chemistry process.

Clause 6. The sensor of Clause 5, wherein the coupling chemistry process includes a silane coupling agent.

Clause 7. The sensor of Clause 5, wherein the coupling chemistry process includes a glutaraldehyde conjugation crosslinker.

Clause 8. The sensor of Clause 5, wherein the coupling chemistry process includes an NHS-EDC carbodiimide crosslinking chemistry.

Clause 9. The sensor of Clause 4, wherein the hydrophobic components include one of alkanes, fats, fluorocarbons, and fluorinated molecules.

Clause 10. The sensor of Clause 4, wherein the clickable components include clickable groups of one of azide, alkyne, thiol, alkene, tetrazine, trans-cyclooctene, bicyclo [6.1.0]nonyne, Dibenzocyclooctyne, and Trans-Cyclooctene.

Clause 11. The sensor of Clause 4, wherein the click chemistry reaction occurs in aqueous solution.

Clause 12. The sensor of Clause 1, wherein the binding material includes a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials.

Clause 13. The sensor of Clause 1, wherein the change of the initial surface energy of at least the portion of the plurality of surfaces of the plurality of walls is visually detectable with an instrument.

Clause 14. The sensor of Clause 1, wherein the change of the initial surface energy of at least the portion of the plurality of surfaces of the plurality of walls is visually detectable with a naked eye.

Clause 15. The sensor of Clause 1 further comprising a colorimetric reporter, wherein the change of the initial surface energy of at least the portion of the plurality of surfaces of the plurality of walls is visually detectable with a color change.

Clause 16. A method of manufacturing a sensor for detecting an analyte of interest in a fluid sample, the method comprising:

providing a structure that includes a plurality of walls that define a plurality of air gaps in the structure, wherein the plurality of walls include a plurality of surfaces;

coating the plurality of walls with a hydrophobic clickable layer;

coating the plurality of walls with a binding material to bind to an analyte of interest; and wherein an initial surface energy of at least a portion of the plurality of surfaces of the plurality of walls changes when the analyte of interest binds with the binding material.

Clause 17. The method of Clause 16, wherein the structure includes at least one of a micrometer scaled structure and a nanometer scaled structure.

Clause 18. The method of Clause 17, wherein at least one of the micrometer scaled structure and the nanometer scaled structure includes a reentrant structure.

Clause 19. The method of Clause 16, wherein the hydrophobic clickable layer includes a hydrophobic component to enable wetting based sensing, wherein the hydrophobic clickable layer further includes clickable components to immobilize the binding material via a click chemistry reaction.

Clause 20. The method of Clause 19, wherein the hydrophobic component and the clickable components are co-immobilized on the plurality of walls via a coupling chemistry process.

Clause 21. The method of Clause 20, wherein the coupling chemistry process includes one of a silane coupling agent, a glutaraldehyde conjugation crosslinker, and an NHS-EDC carbodiimide crosslinking chemistry.

Clause 22. The method of Clause 19, wherein the hydrophobic components include one of alkanes, fats, fluorocarbons, and fluorinated molecules.

Clause 23. The method of Clause 19, wherein the clickable components include clickable groups of one of azide, alkyne, thiol, alkene, tetrazine, trans-cyclooctene, bicyclo [6.1.0]nonyne, Dibenzocyclooctyne, and Trans-Cyclooctene.

Clause 24. The method of Clause 19, wherein the click chemistry reaction occurs in aqueous solution.

Clause 25. The method of Clause 16, wherein the binding material includes a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials.

Clause 26. The method of Clause 16, wherein the change of the initial surface energy of at least the portion of the plurality of surfaces of the plurality of walls is detectable with an instrument.

Clause 27. The method of Clause 16, wherein the change of the initial surface energy of at least the portion of the plurality of surfaces of the plurality of walls is visually detectable with a naked eye.

Clause 28. The method of Clause 16, further comprising providing a colorimetric reporter, wherein the change of the initial surface energy of at least the portion of the plurality of surfaces of the plurality of walls is visually detectable with a color change via the colorimetric reporter.

Clause 29. A method of detecting an analyte of interest, the method comprising:

contacting the sensor of Clause 1 with a sample;

changing an initial surface energy of at least a portion of the plurality of surfaces of the plurality of walls when the analyte of interest is present in the sample; and transitioning between a first mode and a second mode based upon, at least in part, changing the initial surface energy.

Clause 30. A sensor for detecting an analyte of interest in a sample, the sensor comprising:

a structural component grown on a surface from an initiator associated with a nucleic acid linker that is tethered to the surface, wherein a color of the surface changes upon growth of the structural component;

a surface associated with a ribonucleoprotein (RNP) complex that includes:

a CRISPR associated (Cas) nuclease;

a guide RNA (gRNA) that includes a region that binds to the Cas nuclease, and a region that is complementary to a target nucleic acid sequence; and wherein, when the target nucleic acid sequence contacts the gRNA, the gRNA binds to the target nucleic acid sequence, the RNP complex cleaves the nucleic acid linker and releases the structural component grown on the surface, and produces a detectable signal indicative of the target nucleic acid sequence being present.

Clause 31. The sensor of Clause 30, wherein the structural component is a thin film.

Clause 32. The sensor of Clause 30, wherein the structural component is one of a patterned nanostructure and a nanoparticle.

Clause 33. The sensor of Clause 30, wherein the initiator is a polymerization initiator.

Clause 34. The sensor of Clause 30, wherein the nucleic acid linker is one of a single-stranded DNA (ssDNA), double-stranded DNA (dsDNA), and RNA.

Clause 35. The sensor of Clause 30, wherein the target nucleic acid is one of a single-stranded DNA (ssDNA), double-stranded DNA (dsDNA), and RNA.

Clause 36. The sensor of Clause 30, wherein the Cas nuclease is a type V Cas nuclease.

Clause 37. The sensor of Clause 36, wherein the type V Cas nuclease is one of Cas12a (Cpf1), Cas12b (C2c1), Cas12d, Cas12f (Cas14), and Cas12g.

Clause 38. The sensor of Clause 30, wherein the Cas nuclease is a type VI Cas nuclease.

Clause 39. The sensor of Clause 38, wherein the type VI Cas nuclease is one of Cas13a (C2c2), Cas13b, and Cas13d.

Clause 40. The sensor of Clause 30, wherein the detectable signal is visually detected by an instrument.

Clause 41. The sensor of Clause 30, wherein the detectable signal is visually detected by a naked eye.

Clause 42. The sensor of Clause 30, wherein the detectable signal is generated from destruction of at least a portion of a structural color indicator.

Clause 43. A method of detecting an analyte of interest, the method comprising:

contacting the sensor of Clause 30 with a sample; and when the analyte of interest is present in the sample:

cleaving the nucleic acid linker;

releasing the structural component grown on the surface; and producing a detectable signal indicative of the target nucleic acid sequence being present in the sample.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A sensor for detecting an analyte of interest in a fluid sample, the sensor comprising:

a structure including a plurality of walls that define a plurality of air gaps in the structure, wherein the plurality of walls include a plurality of surfaces;

a hydrophobic clickable layer, wherein the hydrophobic clickable layer is coated on the plurality of walls;

a binding material, where the binding material is coated on the plurality of walls to bind to an analyte of interest; and wherein an initial surface energy of at least a portion of the plurality of surfaces of the plurality of walls changes when the analyte of interest binds with the binding material.

2. The sensor of claim 1, wherein the structure includes at least one of a micrometer scaled structure and a nanometer scaled structure.

3. The sensor of claim 2, wherein at least one of the micrometer scaled structure and the nanometer scaled structure includes a reentrant structure.

4. The sensor of claim 1, wherein the hydrophobic clickable layer includes a hydrophobic component to enable wetting based sensing, wherein the hydrophobic clickable layer further includes clickable components to immobilize the binding material via a click chemistry reaction.

5. The sensor of claim 4, wherein the hydrophobic component and the clickable components are co-immobilized on the plurality of walls via a coupling chemistry process.

6. The sensor of claim 5, wherein the coupling chemistry process includes a silane coupling agent.

7. The sensor of claim 5, wherein the coupling chemistry process includes a glutaraldehyde conjugation crosslinker.

8. The sensor of claim 5, wherein the coupling chemistry process includes an NHS-EDC carbodiimide crosslinking chemistry.

9. The sensor of claim 4, wherein the hydrophobic component includes one of alkanes, fats, fluorocarbons, and fluorinated molecules.

10. The sensor of claim 4, wherein the clickable components include clickable groups of one of azide, alkyne, thiol, alkene, tetrazine, trans-cyclooctene, bicyclo[6.1.0]nonyne, Dibenzocyclooctyne, and Trans-Cyclooctene.

11. The sensor of claim 4, wherein the click chemistry reaction occurs in aqueous solution.

12. The sensor of claim 1, wherein the binding material includes a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials.

13. The sensor of claim 1, wherein the change of the initial surface energy of at least the portion of the plurality of surfaces of the plurality of walls is visually detectable with an instrument.

14. The sensor of claim 1, wherein the change of the initial surface energy of at least the portion of the plurality of surfaces of the plurality of walls is visually detectable with a naked eye.

15. The sensor of claim 1 further comprising a colorimetric reporter, wherein the change of the initial surface energy of at least the portion of the plurality of surfaces of the plurality of walls is visually detectable with a color change.

16. A method of manufacturing a sensor for detecting an analyte of interest in a fluid sample, the method comprising:

providing a structure that includes a plurality of walls that define a plurality of air gaps in the structure, wherein the plurality of walls include a plurality of surfaces;

coating the plurality of walls with a hydrophobic clickable layer;

coating the plurality of walls with a binding material to bind to an analyte of interest; and wherein an initial surface energy of at least a portion of the plurality of surfaces of the plurality of walls changes when the analyte of interest binds with the binding material.

17. The method of claim 16, wherein the structure includes at least one of a micrometer scaled structure and a nanometer scaled structure.

18. The method of claim 17, wherein at least one of the micrometer scaled structure and the nanometer scaled structure includes a reentrant structure.

19. The method of claim 16, wherein the hydrophobic clickable layer includes a hydrophobic component to enable wetting based sensing, wherein the hydrophobic clickable layer further includes clickable components to immobilize the binding material via a click chemistry reaction.

20. The method of claim 19, wherein the hydrophobic component and the clickable components are co-immobilized on the plurality of walls via a coupling chemistry process.

21. The method of claim 20, wherein the coupling chemistry process includes one of a silane coupling agent; a glutaraldehyde conjugation crosslinker, and an NHS-EDC carbodiimide crosslinking chemistry.

22. The method of claim 19, wherein the hydrophobic component includes one of alkanes, fats, fluorocarbons, and fluorinated molecules.

23. The method of claim 19, wherein the clickable components include clickable groups of one of azide, alkyne, thiol, alkene, tetrazine, trans-cyclooctene, bicyclo[6.1.0]nonyne, Dibenzocyclooctyne, and Trans-Cyclooctene.

24. The method of claim 19, wherein the click chemistry reaction occurs in aqueous solution.

25. The method of claim 16, wherein the binding material includes a plurality of molecular recognition receptors that include at least one of molecularly-imprinted polymer (MIPs), aptamers, slow off-rate modified aptamers (SOMAmers), affirmers, antibodies, peptides, deoxyribonucleic acid (DNA), ribonucleic acid (RNA), peptide nucleic acid (PNA), oligonucleotides, coordination complex, metal organic framework (MOF) materials, and porous coordination polymer materials.

26. The method of claim 16, wherein the change of the initial surface energy of at least the portion of the plurality of surfaces of the plurality of walls is detectable with an instrument.

27. The method of claim 16, wherein the change of the initial surface energy of at least the portion of the plurality of surfaces of the plurality of walls is visually detectable with a naked eye.

28. The method of claim 16, further comprising providing a colorimetric reporter, wherein the change of the initial surface energy of at least the portion of the plurality of surfaces of the plurality of walls is visually detectable with a color change.

29. A method of detecting an analyte of interest, the method comprising:

contacting the sensor of claim 1 with a sample;

changing an initial surface energy of at least a portion of the plurality of surfaces of the plurality of walls when the analyte of interest is present in the sample; and transitioning between a first mode and a second mode based upon, at least in part, changing the initial surface energy.

* * * * *